United States Patent [19]

Scannon et al.

[11] Patent Number: 4,916,213

[45] Date of Patent: Apr. 10, 1990

[54] RIBOSOMAL INHIBITING PROTEIN-IMMUNOGLOBULIN CONJUGATES WITH SPECIFICITY FOR TUMOR CELL SURFACE ANTIGENS, AND MIXTURES THEREOF

[75] Inventors: Patrick J. Scannon, Davis, Calif.; Robert W. Baldwin, Long Eaton, England; Vera S. Byers, San Francisco, Calif.

[73] Assignee: Xoma Corporation, Berkeley, Calif.

[21] Appl. No.: 206,968

[22] Filed: Jun. 8, 1988

Related U.S. Application Data

[63] Continuation of Ser. No. 896,999, Aug. 15, 1986, which is a continuation-in-part of Ser. No. 875,256, Jun. 17, 1986, Pat. No. 4,708,862, which is a continuation of Ser. No. 468,193, Feb. 22, 1983.

[51] Int. Cl.$^4$ ............... A61K 39/395; C12N 15/00; C07K 15/14

[52] U.S. Cl. ................... 530/391; 530/387; 530/389; 530/806; 530/808; 530/828; 435/240.27; 435/172.2; 424/85.91; 424/85.8

[58] Field of Search ............ 530/387, 389, 390, 391, 530/392, 806, 828; 424/85.8, 87; 435/240.27, 68

[56] References Cited

U.S. PATENT DOCUMENTS

| | | | |
|---|---|---|---|
| 4,146,603 | 3/1979 | Davidson et al. | 424/85 |
| 4,172,124 | 10/1979 | Koprowsi et al. | 935/95 |
| 4,340,535 | 7/1982 | Voisin et al. | 530/390 |
| 4,349,528 | 9/1982 | Koprowski et al. | 424/85 |
| 4,350,626 | 9/1982 | Masuho et al. | 530/390 |
| 4,414,148 | 11/1983 | Jansen et al. | 530/389 |
| 4,590,071 | 5/1986 | Scannon et al. | 530/391 |

OTHER PUBLICATIONS

Gilliland, D. G. et al., P.N.A.S., 77, 4539–4543, (1980).
Vitetta, E. S. et al., Science, 219, 644–650 (1983).
Jansen et al., Immunol Rev., 62, 185, (1982).
Woodbury et al., P.N.A.S., 77(4), 2183–2187 (1980).
Thorpe et al., Immunol Rev., (1982), 62, pp. 119–158, (note pp. 137–138).
Griffin et al., TNCI, 69(4), 799–805, (1982).
Watanabe et al., J. Pharm. Dyn., 7, 593–603, (1984).
Embleton et al., Br. J. Cancer (1981) 43:582–7.
Farrands et al., Lancet (1982) 2:397–400.
Pimm et al., Int. J. Cancer (1982) 30:75–85.
Price et al., Br. J. Cancer (1982) 44:601–10.
Embleton et al., Br. J. Cancer (1983) 47:43–9.
Garnett, et al., Int. J. Cancer (1983) 31:661–70.
Baldwin, et al., Bull. Cancer (1983) 70:132–6.
Pelham, et al., Cancer Immunol. Immunother. (1983) 15:210–6.
Baldwin and Pimm, Cancer Metastasis Rev. (1983) 2:89–106.
Farrands, et al., J. Bone Joint Surg. (1983) 65:638–4.
Price et al., Scand. J. Immunol. (1983) 18:411–20.
Embleton et al., Br. J. Cancer (1984) 49:559–65.
Armitage et al., Br. J. Surg. (1984) 71:407–12.
Pimm and Baldwin, Eur. J. Cancer Clin. Oncol. (1984) 20:515–24.

(List continued on next page.)

Primary Examiner—Margaret Moskowitz
Assistant Examiner—Jeff Kushan
Attorney, Agent, or Firm—Townsend and Townsend

[57] ABSTRACT

Novel compositions and methods are provided for the treatment of cancer employing monoclonal antibodies (MoAbs) conjugated to a toxin. According to the present invention, MoAbs defining epitopes on either a tumor associated glycoprotein antigen of about 72 kD m.w. or on carcinoembryonic antigen conjugated to a ribosomal inhibiting protein, or the like, are employed either alone or in combination as cytotoxic agents in the treatment of various cancers including, but not limited to, colorectal carcinoma, ovarian carcinoma and osteogenic sarcoma.

Hydridomas XMMCO-791 and XMMCO-228 were deposited with the A.T.C.C. on Aug. 14, 1986 and given A.T.C.C. Accession Nos. HB 9173 and HB 9174, respectively.

28 Claims, 3 Drawing Sheets

OTHER PUBLICATIONS

Price, et al., *FEBS Lett.* (1984) 171:31-5.
Price et al., *Br. J. Cancer* (1984) 49:809-12.
Gallego et al., *Int. J. Cancer* (1984) 33:737-44.
Flannery et al., *Eur. J. Cancer Clin. Oncol.* (1984) 20:791-8.
Campbell et al., *Int. J. Cancer* (1984) 34:31-7.
Baldwin et al., *Symp. Fundam. Cancer Res.* (1983) 36:437-55.
Embleton et al., *Behring Inst. Mitt.* (1984) 74:108-11.
Embleton et al., *Behring Inst. Mitt.* (1984) 74:35-8.
Pimm et al., *Behring Inst. Mitt.* (1984) 74:80-6.
Williams et al., *Clin. Oncol.* (1984) 10:375-81.
Symonds et al., *Br. J. Obstet Gynaecol.* (1985) 92:270-6.
Rowland et al., *Cancer Immunol. Immunother.* (1985) 19:1-7.
Pimm et al., *Cancer Immunol. Immunothen.* (1985) 19:18-21.
Perkins et al., *Eur. J. Nucl. Med.* (1985) 10:296-301.
Pimm et al., *J. Nucl. Med.* (1985) 26:1011-23.
Pimm et al., *Eur. J. Nucl. Med.* (1985) 11:300-4.
Pimm et al., *ICRS Med. Sci.* (1985) 13:499-500.
Price et al., *ICRS Med. Sci.* (1985) 13:366-7.
Armitage et al., *Nucl. Med. Commun.* (1985) 6:623-31.
Durrant et al., *Br. J. Cancer* (1986) 53:37-45.
Garnett and Baldwin, *Cancer Res.* (1986) 46:2407-12.

THERAPY OF MICE BEARING XENOGRAFTS OF SARCOMA 791T
WITH XMMCO-791-RTA
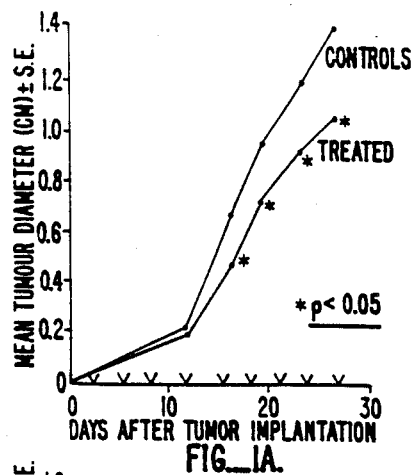
FIG._1A.
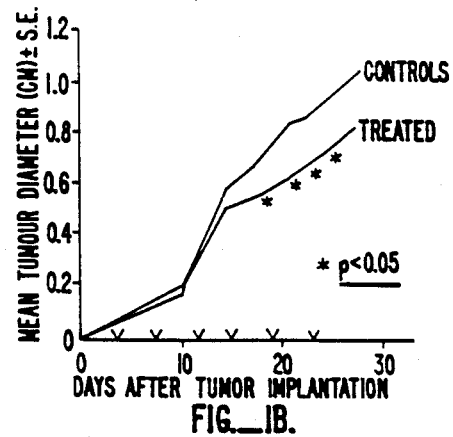
FIG._1B.
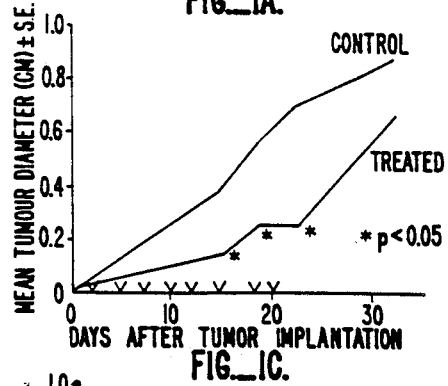
FIG._1C.
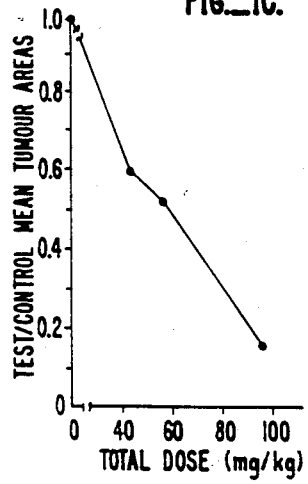
FIG._1D.
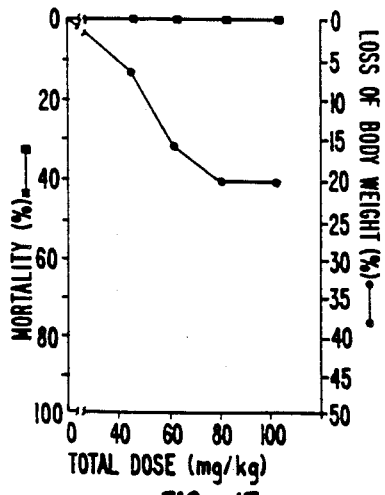
FIG._1E.

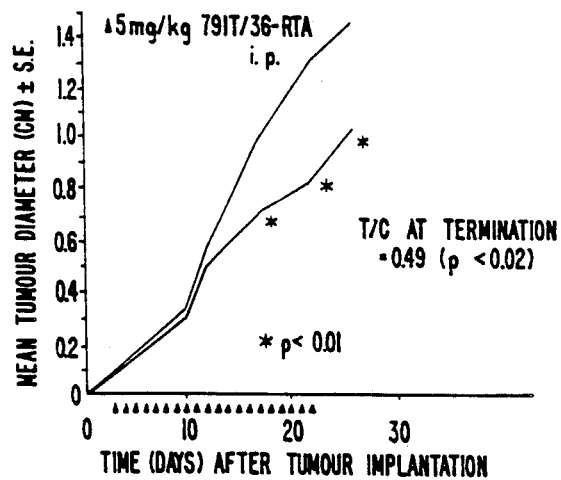
FIG._2.
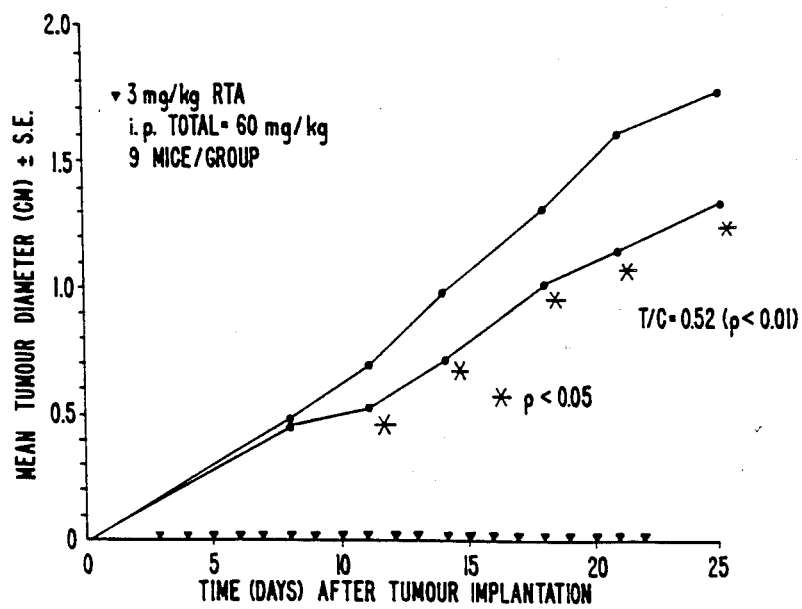
FIG._3.

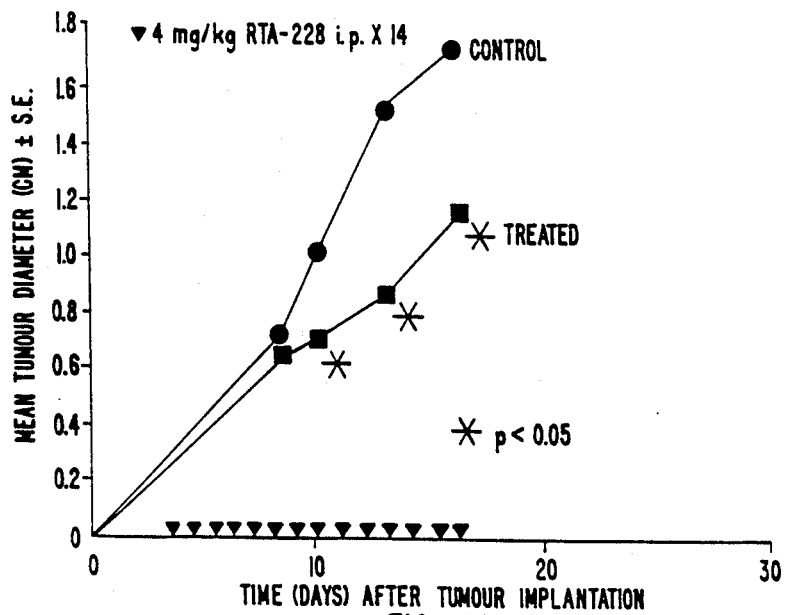
FIG._4A.
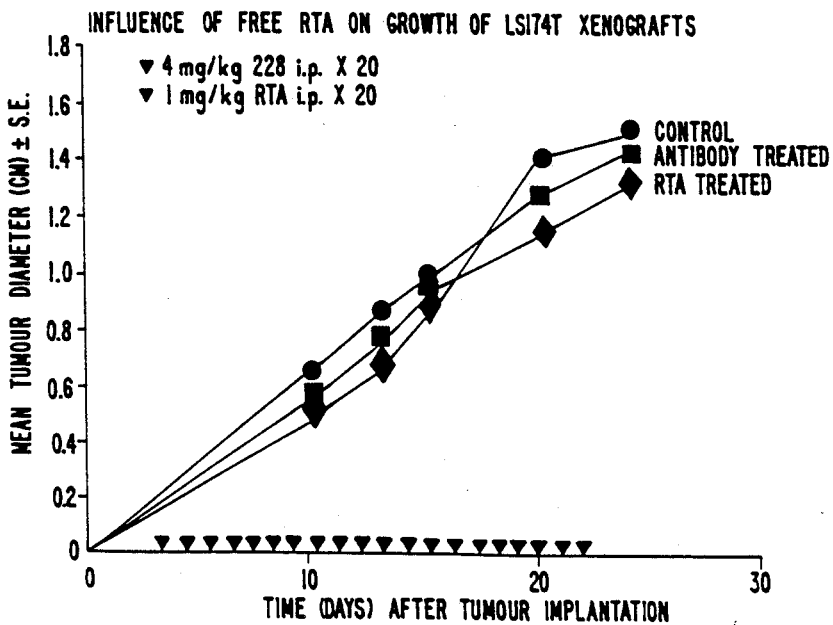
FIG._4B.

RIBOSOMAL INHIBITING PROTEIN-IMMUNOGLOBULIN CONJUGATES WITH SPECIFICITY FOR TUMOR CELL SURFACE ANTIGENS, AND MIXTURES THEREOF

CROSS-REFERENCE TO RELATED APPLICATION

This application is a continuation of U.S. application Ser. No. 896,999, filed Aug. 15, 1986, now abandoned which is a continuation-in-part of U.S. application Ser. No. 06/875,256, filed June 17, 1986, now U.S. Pat. No. 4,708,862 which is a continuation of U.S. application Ser. No. 06/468,193, filed Feb. 22, 1983.

BACKGROUND OF THE INVENTION

Field of the Invention

The present invention relates generally to cancer therapy and, more particularly, to the treatment of colorectal and ovarian carcinoma and osteogenic sarcoma with cytotoxic conjugates of monoclonal antibodies (MoAbs) and ribosomal inhibiting proteins (RIPs).

Colorectal cancer is the second most common cause of death from malignancy in the Western world. The American Cancer Society estimates that there were 138,000 old cases of colorectal cancer and 59,900 patients died from the disease in 1985. The outlook for patients with colorectal disease has remained essentially unaltered over the last 30 years, with the five-year survival being on the order of 30%. A major factor contributing to this is the lack of effective treatment for the disease once it has spread beyond the bowel wall, since surgery during the early stages of the disease offers the only prospect of cure.

Unfortunately, the majority of patients have disseminated disease at the time of initial surgery, primarily with overt or occult hepatic and lymph node metastases.

Despite numerous trials of chemotherapy, the only single agent shown to have any significant effect is 5-fluorouracil; its response rate is inadequate and treatment with it rarely influences the ultimate outcome. Combination chemotherapy and intrahepatic arterial infusion are being investigated but currently do not represent effective treatments.

Cancer of the ovary accounts for roughly 5% of all cancers in women and is the sixth leading cancer in women. Although surgery is curative if this lesion is detected early enough, the mortality associated with this disease has not improved appreciably in the last 25 years.

Ultrasound, laparoscopy or peritoneoscopy, and CAT scan are of limited value in the diagnosis of ovarian carcinoma. Serum markers such as carcinoembryonic antigen and placental alkaline phosphatase as well as some newly defined antigens are found in the blood of some patients with adenocarcinoma, although there is no universal marker. Surgery with biopsy is the only definitive way of diagnosing ovarian carcinoma.

Surgery is currently the only cure for ovarian carcinoma, and is only curative if the tumor has not spread. Radioisotope implants, x-ray irradiation, and chemotherapy are of limited use in the management of ovarian carcinoma.

The most important prognostic indication is the extent of spread of the tumor at the time of diagnosis and surgery. Stage I ovarian carcinoma (growth limited to the ovaries) has an overall 5-year survival rate of approximately 80%, Stage II (growth involving ovaries with pelvic extension) has a 5-year survival rate of 40%, Stage III (growth involving ovaries with extension to small bowel or omentum) has a 5-year survival rate of 10%, and Stage IV (distant metatases) has a 5-year survival rate 37% of (1973–80), relatively the same as for 1960–63 (32%).

Imaging studies of ovarian carcinoma with radiolabelled MoAbs have been performed to a limited degree in human and animal systems. Tumors as small as 1 mm in diameter in mice bearing xenografts of human ovarian cancer have been imaged. The same study also detected tumors in 8 out of 10 patients with ovarian cancer.

Osteogenic sarcoma (OS) is the most common primary bone tumor. Although surgery can be curative if this lesion is detected early enough, the usual course of this disease in 80%–85% of patients is multiple pulmonary metastases and death within two years of diagnosis. These metastases are often present but usually not large enough to be seen at diagnosis of the primary tumor.

Amputation is the treatment of choice for OS. Limb salvage procedures have been performed, such as en-block resection and prosthetic replacement. Overall survival for limb salvage is either as poor or worse than with amputation.

Radiation treatment has not been shown to prevent OS metastases.

Most recent trials note survival rates of over 50% at 5 years for patients treated by widely diverse adjunctive methods. The question is whether all of these widely diverse forms of treatment are effective or if there is a change in the natural history of the disease.

Imaging studies of OS with radiolabelled MoAbs have been performed to a limited degree in human and animal systems. Human OS xenografts have been image in nude mice using an anti-OS MoAb labelled with $^{131}$I.

Because of the extent of these three forms of cancer, there is a need for new compositions and methods to treat primary, recurrent and metastatic disease.

DESCRIPTION OF THE RELEVANT LITERATURE

Embleton et al., *Br. J. Cancer* (1981) 43: 582–7, report preparation of a hybridoma against osteogenic sarcoma cell line 791T, and binding properties of the resulting MoAb with respect to a variety of cell types.

Farrands et al., *Lancet* (1982) 2: 397–400, describe radioimaging of human colorectal cancers using MoAb 791T radiolabelled with $^{131}$I.

Pimm et al., *Int. J. Cancer* (1982) 30: 75–85, describe in vitro localization of osteogenic sarcoma xenografts in mice using radiolabelled 791T MoAbs.

Price et al., *Br. J. Cancer* (1982) 46: 610-10, report on complement-dependent cytotoxicity of two anti-791T osteogenic sarcoma MoAbs against human tumor cell lines, and failure of one of these MoAbs to inhibit 791T tumor xenografts in mice.

Embleton et al., *Br. J. Cancer* (1983) 47: 43–9, describe coupling of the drug vindesine to 791T MoAbs, and in vitro cytotoxicity testing of the conjugate.

Garnett, et al., *Int. J. Cancer* (1983) 31: 661–70, describe in vitro cytotoxicity testing of a 791T MoAb methotrexate conjugate.

Baldwin, et al., *Bull. Cancer* (1983) 70: 132–6, describe the use of radiolabelled 791T MoAb to detect colorectal carcinoma, and evaluate the MoAb for targeting anti-tumor agents including cytotoxic drugs and immunomodulating agents.

Pelham, et al., *Cancer Immunol. Immunother.* (1983) 15: 210–6, describe coupling of interferon to the MoAb 791T, and the retention of biologic activity of both entities of the conjugate.

Baldwin and Pimm, *Cancer Metastasis Rev.* (1983) 2: 89–106, summarize a series of radioimaging experiments using $^{131}$I labelled 791T MoAbs to localize human tumor xenografts in mice.

Farrands et al., *J. Bone Joint Surg.* (1983) 65: 638–4, report on detection of a primary osteogenic sarcoma in a patient using $^{131}$I labelled 791T MoAbs.

Price et al., *Scand. J. Immunol.* (1983) 18: 411–20, report on the identification of an antigen on mitogen-stimulated peripheral blood mononuclear cells using the MoAb 791T, and the characterization of this antigen as being identical to the 791T MoAb-defined antigen found on osteogenic sarcoma cells.

Embleton et al., *Br. J. Cancer* (1984) 49: 559–65, describe treatment of osteogenic sarcoma cells with a methotrexate/791T MoAb conjugate at toxic concentrations which allowed "escape" of some tumor colonies, which were then evaluated for growth potential.

Armitage et al., *Br. J. Surg* (1984) 71: 407–12, report on the imaging of gastrointestinal cancers in patients and discuss radiolabelled 791T MoAb uptake in malignant and non-malignant tissue.

Pimm and Baldwin, *Eur J. Cancer Clin. Oncol.* (9184) 20: 515–24, describe the extent and rate of localization of radiolabelled 791T MoAb in osteogenic sarcoma xenografts in mice.

Price et al., *FEBS Lett.* (1984) 171: 31–5, report on the characterization of the cell surface antigen p72 with which the MoAb 791T reacts.

Price et al., *Br. J. Cancer* (1984) 49: 809–12, review radioimaging studies using 791T and discuss localization of the antibody within the tumor.

Gallego et al., *Int. J. Cancer* (1984) 33: 737–44, report on the coupling of the drug daunomycin to the MoAb 791T, using four different coupling procedures, and evaluate the four conjugates for cytotoxicity to tumor cells.

Flannery et al., *Eur. J. Cancer Clin. Oncol.* (1984) 20: 791–8, describe coupling of interferon to the MoAb 791T, and the activation of NK cells by this conjugate.

Campbell et al., *Int. J. Cancer* (1984) 34: 31–7, describe the analysis of expression on various cell lines of the antigen with which the MoAb 791T reacts.

Baldwin et al., *Symp. Fundam. Cancer Res.* (1983) 36: 437–55, describe radioimaging of primary and metastatic colorectal carcinomas in patients using radiolabelled 791T MoAb.

Embleton et al., *Behring Inst. Mitt.* (1984) 74: 108–11, summarize cytotoxicity testing of a vindesine/791T MoAb conjugate and a methotrexate/791T MoAb conjugate.

Embleton et al., *Behring Inst. Mitt.* (1984) 74: 35–8, summarize reactivity of two anti-human tumor MoAbs, 791T and C14/1/46.

Pimm et al., *Behring Inst. Mitt.* (1984) 74: 80–6, describe detection of primary and metastatic colorectal carcinoma in patients using $^{131}$I labelled 791T MoAb.

Williams et al., *Clin. Oncol.* (1984) 10: 375–81, describe detection of primary and metastatic mammary carcinoma in patients using $^{131}$I labelled 791T MoAb.

Symonds et al., *Br. J. Obstet Gynaecol.* (1985) 92: 270–6, describe preliminary results of detection of ovarian tumors in patients using $^{131}$I labelled 791T MoAb.

Rowland et al., *Cancer Immunol. Immunother.* (1985) 19: 1, report formation of four vindesine-MoAb conjugates, including the MoAb 791T, and compare the conjugates, free vindesine, and free MoAb for their ability to inhibit tumor cell growth.

Pimm et al., *Cancer Immunol. Immunothen.* (1985) 19: 18–21, describe localization of a primary osteogenic sarcoma tumor in situ using $^{131}$I-labelled 791T MoAb, and subsequent localization of xenografts of the tumor in mice.

Perkins et al., *Eur. J. Nucl. Med.* (1985) 10: 296–301, report on a method of labelling the MoAb 791T with $^{111}$In.

Pimm et al., *J. Nucl. Med.* (1985) 26: 1011–23, describe characteristics of the blood survival of $^{131}$I and $^{111}$In-labelled 791T MoAbs in patients with colorectal carcinoma, ovarian carcinoma, and osteogenic sarcoma in tumor imaging studies.

Pimm et al., *Eur. J. Nucl. Med.* (1985) 11: 300–4, describe comparison of the blood, tumor and whole-body levels of $^{131}$I and $^{111}$In labelled 791T MoAb in mice with human tumor xenografts.

Pimm et al., *ICRS Med. Sci.* (1985) 13: 499–500, describe the production of anti-idiotypic antibodies to 791T MoAb following administration of radiolabelled 791T MoAb in a series of patients.

Pimm et al., *ICRS Med. Sci.* (1985) 13: 366–7, describe a solid-phase micro-radioimmunoassay as a means of measuring MoAb reactivity with antigens, using 791T as an example.

Armitage et al., *Nucl. Med. Commun.* (1985) 6: 623–31, describe imaging of primary and metastatic colorectal carcinoma using $^{111}$In labelled 791T MoAb.

Durrant et al., *Br. J. Cancer* (1986) 53: 37–45, report on the localization of the MoAb 791T within xenografts derived from colorectal adenocarcinomas.

Garnett and Baldwin, *Cancer Res.* (1986) 46: 2407–12, describe improved synthesis of a drug-carrier-MoAb conjugate using methotrexate and 791T.

SUMMARY OF THE INVENTION

Novel compositions and methods are provided form the treatment of cancer employing monoclonal antibodies (MoAbs) conjugated to a toxin. According to the present invention, MoAbs defining epitopes on either a tumor associated glycoprotein antigen of about 72 kD m.w. or on carcinoembryonic antigen conjugated to a ribosomal inhibiting protein, or the like, are employed either alone or in combination as cytotoxic agents in the treatment of various cancers including, but not limited to, colorectal carcinoma, ovarian carcinoma and osteogenic sarcoma.

BRIEF DESCRIPTION OF THE FIGURES

FIG. 1 is a graphic illustration of the results obtained in the therapy of mice-bearing xenografts of osteogenic sarcoma 791T cells with XMMCO-791-RTA;

FIG. 2 is a graphic illustration of the results obtained in the therapy of mice bearing xeongrafts of colorectal carcinoma C170 cells with XMMCO-791-RTA at a dose of 5 mg/kg/day;

FIG. 3 is a graphic illustration of the results obtained in the therapy of mice bearing xenografts of colorectal carcinoma C170 cells with XMMCO-791-RTA at a dose of 3 mg/kg/day; and FIG. 4 is a graphic illustration of the influence of free RTA and XMMCO-228-RTA on the growth of colorectal carcinoma LS174T cell xenografts.

DETAILED DESCRIPTION OF THE PREFERRED EMBODIMENTS

The present invention employs cytotoxic conjugates for the treatment of various forms of cancer, including colorectal carcinoma, ovarian carcinoma and osteogenic sarcoma. These novel conjugates are comprised of monoclonal antibodies or binding fragments thereof, collectively termed immunoglobulins, boundto a cytotoxin. These compositions are administered to a cancer cell host in order to destroy cancer cells while doing minimal damage to normal tissue.

The immunoglobulins of the present invention are employed as targeting agents for directing cytotoxic agents to specific cancer cells within a cancer cell host. According to the present invention, immunoglobulins which define an epitope on a 72 kilodalton (kD) glycoprotein antigen and immunoglobulins which define an epitope on carcinoembryonic antigen (CEA) are employed as targeting agents. One or both of these antigens are present on a variety of cancers incliuding, but not limited to, colorectal carcinoma, ovarian carcinoma and osteogenic sarcoma.

These targeting immunoglobulins are bound to a variety of cytotoxic agents, generally ribosomal inhibiting proteins, more particularly, the A chain of ricin or the A chain of abrin. The A chain of ricin has been successfully employed in cytotoxic conjugates as disclosed in U.S. Pat. No. 4,590,071, the disclosures of which are hereby incorporated by reference.

The immunoglobulin and toxin are generally bound by a covalent bond, more particularly a disulfide bond, but may be joined by any chemical bond which allows the toxin to travel to the target cell with the immunoglobulin. Other methods for achieving such a bond are well-known to those skilled in the art. The only criteria is that the bond must be achieved in a manner which does not significantly decrease the binding affinity of the immunoglobulin for its epitope.

The present cytotoxic conjugates may be administered to a cancer cell host either singly or in a cocktail containing two or more conjugate formulations. Cocktails are particularly important in the treatment of heterogenious tumor cell populations wherein targeting of multiple antigens is critical.

The cytotoxic conjugates of the present invention may be administered to a cancer cell host by any convenient method. Pharmaceutical compositions employing the subject conjugates may be administered parenterally, i.e., intravenously, intraparitoneally, or the like. Thus, this invention provides compositions for parenteral administration which comprise a solution of pyrogen free, cytotoxic conjugates, or a cocktail thereof, dissolved in an acceptable carrier, preferably an aqueous carrier. A variety of aqueous carriers can be used, e.g., water, buffered water, 0.4% saline, 0.3% glycine, or the like. These solutions are sterile and generally free of particulate matter. These compositions may be sterilized by conventional, well-known filtration sterilization techniques. The compositions may contain pharmaceutically acceptable auxiliary substances as required to approximate physiological conditions such as pH adjusting and buffering agents, toxicity adjusting agents, or the like, for example, sodium acetate, sodium chloride, potassium chloride, potassium chloride, calcium chloride, sodium lactate, etc.

The compositions of the present invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss and that use levels may have to be adjusted to compensate.

Single or multiple administrations of the compositions can be carried out with dose levels and pattern being selected by the treating physician. In any event, the pharmaceutical formulation should provide a quantity of conjugate(s) of this invention sufficient to effectively treat the cancer cell host. The dose of conjugate or conjugate cocktail will vary widely, generally from about 0.01 mg/kg/day to 20.0 mg/kg/day, usually about 0.05 mg/kg/day to 10.0 mg/kg/day, and, more particularly, 0.05 mg/kg/day to 5.0 mg/kg/day.

Kits may also be supplied for use with the subject conjugates or cocktails. Thus, the subject compositions may be provided, usually in lyophilized form, either alone or in conjunction with additional chemotherapeutic agents for cancer therapy. These kits may include buffers, such as phosphate buffered saline, other inert ingredients, or the like. The kits may also include specific instructions including suggested protocols for the administration of the subject compositions to a cancer cell host.

The following examples are offered by way of illustration and not limitation.

Experimental

EXAMPLE I—XMMCO-791-RTA CONJUGATES

A. Production of XMMCO-791 Hybidomas

Balb/c mice (Bantin and Kingman, U.K.) were immunized with cultured 791T cells according to the following schedule:

1. Day 0: $1 \times 10^7$ cells were given intraperitoneally (IP) in Hank's balanced salt solution (HBSS);

2. Day 7: $1 \times 10^7$ cells were given IP in HBSS; and

3. Day 21: $2 \times 10^6$ cells were given by intracardiac injection.

The 791T cell line used for immunization was obtained from Dr. Vera S. Byers, University of California, San Francisco. 791T is a human osteogenic sarcoma cell line isolated from the pulmonary metastasis of a 19-year-old Caucasian male. The cell line was characterized as malignant by its ability to grow as a tumor xenograft in nude mice, its lack of contact inhibition in culture and its abnormal nuclear and cytoplasmic morphology.

On day 26 after the initial immunization, spleen cells from immunized mice were aseptically removed. Following procedures as outlined elsewhere (Galfre et al., Nature (1977) 226: 550, which is incorporated by reference), $5 \times 10^7$ spleen cells were fused with an equal number of P3/NSI/1-Ag4-1 cells (A.T.C.C. Accession No. TIB-18) using polyethylene glycol 4000. The P3/NSI/1-Ag4-1 cell line is a non-secreting mouse myeloma cell line of Balb/c origin. This line is resistant to 8-azaguanine and lacks the enzyme hypoxanthine quanine phosphoribosyl transferase so that hypoxanthine-aminopterin-thymidine (HAT) medium becomes toxic, providing a convenient method of selecting unfused parental myeloma cells from the hybridoma population.

Cloning was performed by plating cells at low density in 0.3% agar in RPMI 1640 medium supplemented with 50 mg/ml gentomycin and hypoxanthine-aminopterin-thymidine (HAT) with 10% fetal calf serum, and overlaying a gel of 0.5% agar in the same medium. Spherical colonies were removed by Pasteur pipette. Recloning was performed by the limiting dilution technique, in which less than one hybridoma per three wells of a 96-well microticter plate was plated in the presence of $2 \times 10^4$ peritoneal exudate cells from unimmunized WAB/Not rats. Medium for regular maintenance was identical to the above, except that no aminopterin was included (HT medium).

The antibodies secreted by each clone were assayed for the appropriate specificity by radioimmune binding assay (Embleton et al., *Br. J. Cancer* (1981) 43: 582-87). One clone, designated XMMCO-791 was found to stably secrete monoclonal antibody; the antibody was determined to be of immunoglobulin class IgG2b. Hybridoma XMMCO-791 is presently on deposit with the American Type Culture Collection (A.T.C.C.), 12301 Parklawn Dr., Rockville, MD 20852, U.S.A. The deposit was made on Aug. 14, 1986, and given A.T.C.C. Accession No. HB 9173.

Specific pathogen free (SPF) Balb/c mice (Charles River) were used to culture the hybridoma intraperitoneally. Approximately $2 \times 10^6$ XMMCO-791 hybridoma cells in 0.5 ml of phosphate buffered saline (PBS) pH 7.2 were injected I.P. into pristane primed mice 7 to 21 days post priming. Priming was performed by injecting SPF Balb/c mice I.P. with 0.5 ml Pristane (2,6,10,14-tetramethylpentaclecane). The resultant ascites fluid, collected 10-14 days post injection of hybridomas, contained 1.2 to 1.6 mg/ml of the antibody, as determined by double immunodiffusion.

The antibody in ascites fluid was purified following sterile filtration through a $0.22\mu$ filtering system by loading onto a Staphylococcal protein A column (Staph protein A) and allowed to bind at 4° C., pH 7.5. The effluent was monitored spectrophotometrically until there was no further change of absorbance. The column was then subjected to pH gradient elutions (pH 5.0 and pH 3.0, 0.1M sodium citrate buffer) and the monoclonal antibody collected. Purified antibody was stored frozen following aliquoting and quick freezing.

B. Antibody Binding to Cell Lines

The binding of XMMCO-791 to a large number of cultured human tumor cells and cultured human fibroblasts was compared by various assays to define tumor specific binding. These assays are detailed below. Studies show that there is little binding to normal fibroblasts, granulocytes, red blood cells, or lymphoblastoid cell lines; but there is significant binding to osteogenic sarcoma, colorectal and ovarian carcinoma. Studies described later demonstrate significant binding to freshly disaggregated human colorectal and ovarian carcinoma tumors.

1. $^{125}I$ Protein A-Binding Assay

Target cells in round-bottomed microtest plates were incubated on ice with hybridoma supernatant. The cells were washed and incubated for an additional 1 hour on ice with Protein A (Pharmacia) labeled with $^{125}I$. The cells were washed and dried down. After spraying with a plastic film (Nobecutane), the wells were separated with a band saw and the bound $^{125}I$ measured in a gamma counter.

XMMCO-791 hybridoma supernatants were reacted with cultured cells derived from a range of human tumors and normal fibroblasts. Representative data are summarized in Table I. In tests with 36 malignant cell lines and 9 fibroblast cell lines, XMMCO-791 antibody reacted with 7/13 osteogenic sarcomas; 1/3 lung carcinomas, 1/1 prostate carcinomas, and 1/1 cervical carcinomas. 3/5 colorectal carcinomas also reacted strongly with binding ratios (BR) up to 33.40. Of the fibroblast lines, 1/9 reacted weakly (BR 2.14). Tests were carried out with fibroblasts derived from the donor of the tumor cell line 791T and these target cells did not react with XMMCO-791 (BR 0.99). Peripheral blood mononuclear cells were also negative.

TABLE I

| | | | | | |
|---|---|---|---|---|---|
| Reactivity of XMMCO-791 Monoclonal Antibody Against Cultured Human Cells (Radioimmunoassay) | | | | | |
| | | Mean cpm (± S.D.) with: | | | |
| Tumor Type | Cell Line | P3NS1 supt. | XMMCO-791 | Cpm increment[1] | Binding Ratio[2] |
| Osteogenic sarcoma | 791T | 480 ± 100 | 10,965 ± 378 | 10,485 | 22.84 |
| Osteogenic sarcoma | 706T | 275 ± 44 | 685 ± 260 | 410 | 2.49 |
| Osteogenic sarcoma | 781T | 553 ± 9 | 1,014 ± 105 | 461 | 1.83 |
| Osteogenic sarcoma | 788T | 364 ± 142 | 17,044 ± 1,646 | 16,680 | 46.82 |
| Osteogenic sarcoma | 792T | 358 ± 55 | 443 ± 18 | 85 | 1.23 |
| Osteogenic sarcoma | 803T | 274 ± 14 | 399 ± 30 | 125 | 1.45 |
| Osteogenic sarcoma | 805T | 615 ± 86 | 2,096 ± 28 | 1,481 | 3.41 |
| Osteogenic sarcoma | 836T | 1,071 ± 137 | 835 ± 116 | −236 | 0.78 |
| Osteogenic sarcoma | 845T | 250 ± 30 | 1,373 ± 73 | 1,145 | 5.58 |
| Osteogenic sarcoma | 888T | 860 ± 104 | 926 ± 85 | 66 | 1.08 |
| Osteogenic sarcoma | T278 | 794 ± 36 | 16,490 ± 404 | 15,696 | 20.77 |
| Osteogenic sarcoma | 20S | 1,542 ± 213 | 4,689 ± 341 | 3,147 | 3.04 |
| Osteogenic sarcoma | 393T | 676 ± 20 | 1,110 ± 123 | 434 | 1.64 |
| Colon Carcinoma | HCT8 | 427 ± 177 | 689 ± 52 | 262 | 1.61 |
| Colon Carcinoma | HRT18 | 565 ± 168 | 684 ± 95 | 119 | 1.21 |
| Colon Carcinoma | HT29 | 522 ± 101 | 3,474 ± 177 | 2,952 | 6.66 |
| Colon Carcinoma | LS174T | 266 ± 48 | 3,786 ± 203 | 3,520 | 14.23 |
| Colon Carcinoma | HcLo | 302 ± 12 | 10,087 ± 635 | 9,785 | 33.40 |
| Lung Carcinoma | A427 | 328 ± 152 | 358 ± 27 | 30 | 1.09 |
| Lung Carcinoma | A549 | 566 ± 137 | 2,572 ± 187 | 2,006 | 4.54 |
| Lung Carcinoma | 9812 | 390 ± 8 | 541 ± 46 | 151 | 1.39 |
| Breast Carcinoma | SK Br3 | 1,624 ± 25 | 2,505 ± 258 | 881 | 1.54 |

TABLE I-continued

Reactivity of XMMCO-791 Monoclonal Antibody Against Cultured Human Cells (Radioimmunoassay)

| Tumor Type | Cell Line | Mean cpm (± S.D.) with: P3NS1 supt. | XMMCO-791 | Cpm increment[1] | Binding Ratio[2] |
|---|---|---|---|---|---|
| Breast Carcinoma | 578T | 470 ± 103 | 575 ± 65 | 105 | 1.22 |
| Breast Carcinoma | 734B | 482 ± 431 | 906 ± 133 | 423 | 1.87 |
| Breast Carcinoma | MCF7 | 716 ± 50 | 846 ± 61 | 150 | 1.18 |
| Melanoma | Nk1-4 | 285 ± 36 | 258 ± 70 | 73 | 1.25 |
| Melanoma | Mel-2a | 418 ± 105 | 568 ± 13 | 150 | 1.36 |
| Melanoma | Mel-57 | 560 ± 78 | 544 ± 160 | −16 | 0.97 |
| Melanoma | MeWo | 232 ± 36 | 228 ± 36 | −4 | 0.98 |
| Melanoma | RPMI5966 | 327 ± 94 | 445 ± 191 | 118 | 1.36 |
| Lymphoblastoid Line | Raji | 668 ± 354 | 844 ± 347 | 176 | 1.26 |
|  | K562 | 1,086 ± 171 | 905 ± 115 | −181 | 0.83 |
| Prostate Carcinoma | EB33 | 429 ± 66 | 12,147 ± 378 | 11,718 | 28.3 |
| Bladder Carcinoma | T24 | 285 ± 40 | 429 ± 28 | 144 | 1.50 |
| Cervical Carcinoma | HeLa | 258 ± 18 | 14,257 ± 658 | 13,999 | 55.52 |
| Ovarian Carcinoma | PA1 | 398 ± 69 | 408 ± 51 | 10 | 1.03 |
| Fibroblasts | 181 Sk | 784 ± 184 | 1,682 ± 440 | 898 | 2.14 |
| Fibroblasts | 788 Sk | 1,033 ± 374 | 927 ± 125 | −106 | 0.90 |
| Fibroblasts | 791 Sk | 403 ± 39 | 399 ± 54 | −4 | 0.99 |
| Fibroblasts | 803 Sk | 350 ± 39 | 362 ± 28 | 12 | 1.03 |
| Fibroblasts | 836 Sk | 227 ± 85 | 295 ± 56 | 68 | 1.29 |
| Fibroblasts | 860 | 1,165 ± 38 | 1,624 ± 347 | 459 | 1.39 |
| Fibroblasts | 870 | 404 ± 16 | 443 ± 84 | 39 | 1.09 |
| Fibroblasts | 618 Lu | 500 ± 51 | 538 ± 82 | 38 | 1.09 |
| Fibroblasts | 74 BM | 350 ± 52 | 593 ± 68 | 243 | 1.69 |
| Non-cultured cells:- | RBC | 511 ± 14 | 500 ± 42 | −71 | 0.86 |
| Non-cultured cells:- | Mononuclear cells | 410 ± 112 | 492 ± 115 | 82 | 1.20 |
|  | SRBC | 481 ± 77 | 482 ± 261 | 1 | 1.00 |

[1]CpM for XMMCO-791 minus cpm for P3NS1 supernatant.
[2]CPM for XMMCO-791 divided by cpm for P3NS1 supernatant. A binding ratio of >2 represents significant reactivity. These positive reactions are underlined.

2. Direct Binding Assay with $^{125}$I-Labeled XMMCO-791 Antibody

Tissue culture-derived target cells were aliquoted into round-bottomed microtest plates, sedimented by centrifugation, and incubated for 60 minutes with aliquots of $^{125}$I-XMMCO-791. The cells were washed and dried down. The wells were separated from the plate and bound radioactivity counted (Price MR, et al., 1982; Pimm MV, et al., 1982).

Direct binding of $^{125}$I-labeled XMMCO-791 to a range of tumor cells is shown in Table II and this data is summarized in Table III which expresses target cell binding of XMMCO-791 antibody relative to that with 791T cells. These tests demonstrate that $^{125}$I-XMMCO-791 binds to osteogenic sarcomas 791T and 788T, and to HeLa cells. Binding of $^{125}$I-XMMCO-791 to other cell line derived tumor cells, including lung carcinoma (A427 and A549) and bladder carcinoma (T24), was approximately 10% of that with 791T cells.

3. Flow Cytometry a. Direct Binding of FITC-Labeled XMMCO-791

Target cells were incubated with saturating doses of fluorescein isothiocyanate-labeled XMMCO-791 (FITC-XMMCO-791) and analyzed by flow cytometry. The binding of FITC-XMMCO-791 is expressed as fluorescence units/cell (Price MR, et al., 1983b; Gallego J. et al., 1984; Roe R. et al., 1985).

TABLE II

Binding of $^{125}$I-Labeled XMMCO-791 Monoclonal Antibody to Cultured Human Tumor Cells

| Exp. | Target Cells | $^{125}$I-antibody bound (mean cpm ± SD)[1] |
|---|---|---|
| 1 | None | 413 ± 189 |
|  | Osteogenic sarcoma 791T | 6,301 ± 605* |
|  | Breast carcinoma SKBr3 | 772 ± 61 |
|  | Colon carcinoma HCT8 | 532 ± 157 |
|  | Lung carcinoma A427 | 741 ± 152 |
| 2 | None | 160 ± 44 |
|  | Osteogenic sarcoma 791T | 3,265 ± 425* |
|  | Osteogenic sarcoma 788T | 3,356 ± 163* |
|  | Osteogenic sarcoma 888T | 452 ± 25 |
|  | Bladder carcinoma T24 | 506 ± 40 |
|  | Colon carcinoma HRT18 | 571 ± 60 |
|  | Ovarian carcinoma PA1 | 164 ± 48 |
| 3 | Osteogenic sarcoma 791T | 8,915 ± 51* |
|  | Osteogenic sarcoma 788T | 6,906 ± 25* |
|  | Osteogenic sarcoma 20s | 7,570 ± 112* |
|  | Osteogenic sarcoma 393T | 626 ± 6 |

[1] $2 \times 10^5$ target cells were treated with 0.1 ml $^{125}$I-labeled antibody preparation (50 ng protein) in replicates of four.
*Cpm is significantly higher than cpm with other cell lines within the same test as assessed by the Wilcoxon rank test.

TABLE III

Direct Cell Binding of $^{125}$I-labeled XMMCO-791 Monoclonal Antibody

| Cell Line | Cell Type | Percentage Binding[1] of $^{125}$I-labeled Monoclonal Antibody |
|---|---|---|
| 791T | Osteogenic sarcoma | 100 |
| 788T | Osteogenic sarcoma | 103 |
| 888T | Osteogenic sarcoma | 9 |
| HRT 18 | Colorectal carcinoma | 13 |
| HCT 8 | Colorectal carcinoma | 7 |
| SK Br 3 | Breast carcinoma | 6 |
| A427 | Lung carcinoma | 11 |
| A594 | Lung carcinoma | 12 |
| HeLa | Cervix carcinoma | 86 |
| PA1 | Ovarian carcinoma | 0 |
| T24 | Bladder carcinoma | 11 |

TABLE III-continued

Direct Cell Binding of $^{125}$I-labeled
XMMCO-791 Monoclonal Antibody

| Cell Line | Cell Type | Percentage Binding[1] of $^{125}$I-labeled Monoclonal Antibody |
|---|---|---|
| RPMI 5966 | Melanoma | 13 |

[1]Binding of $^{125}$I-labeled anti-791T/36 monoclonal antibody to various target cell lines is expressed as the percentage of the binding of labeled antibody to 791T tumor cells.

Specificity is demonstrated by mixing unlabeled MoAb with FITC-labeled MoAb and demonstrating that the fluorescence per cell decreased. Titrating FITC-XMMCO-791 antibody against a fixed number of 791T cells indicated that maximum uptake of labeled antibody was obtained at approximately 0.1 µg of antibody per $2 \times 10^5$ cells.

Table IV summarizes tests in which target cells derived from human tumor cell lines were reacted with FITC-XMMCO-791 and analyzed by flow cytometry. The antibody consistently reacted with osteogenic sarcoma 791T and 788T cells; these cells were used as standards for reference purposes. Ovarian carcinoma PA1 cells showed essentially no reactivity with XMMCO-791. All of the tumors listed bound significant amounts of FITC-XMMCO-791, although this was less than that observed with 791T cells. The C146, C168, and C170 cell lines were recently derived from surgical specimens obtained at the Department of Surgery, University Hospital, Queens Medical Centre, Nottingham, U.K. (Director, Professor J. D. Hardcastle). Since these tests were carried out with FITC-XMMCO-791 under saturating conditions, the number of antibody molecules bound/cell can be determined (Roe R., et al., 1985). Thus, colon tumor derived cells bound between $1.6 \times 10^5$ and $2.8 \times 10^5$ antibody molecules/cell compared with a value of $6 \times 10^5$ for osteogenic sarcoma 791T cells.

TABLE IV

Binding of FITC-XMMCO-791 Monoclonal Antibody
with Cultured Human Tumor Cells

| Tumor cell | Mean Fluorescence Units/cell |
|---|---|
| Osteogenic Sarcoma | |
| 791T | 709.3, 722.4, 245 |
| 788T | 368.5 |
| Colon Carcinoma | |
| HCRT18 | 169 |
| LS174T | 172.8, 187.6, 105.2 |
| C146 | 117 |
| C168 | 69 |
| C170 | 88 |
| Ovarian Carcinoma | |
| PA1 | <9 | b. Indirect Membrane Immunofluorescence Assay

Tumor cell lines were incubated with saturating amounts of XMMCO-791 monoclonal antibody, then washed and incubated with FITC-labeled rabbit anti-mouse Ig. The samples were analyzed by flow cytometry (Roe R., et al., 1985). Table V summarizes these tests with results expressed as fluorescence units/cell. The results showed the same pattern as with direct immunofluorescence: maximal binding with osteogenic sarcoma cell lines, intermediate with colon carcinoma cell lines, and low levels with ovarian, bladder, and breast carcinoma cell lines.

The binding of XMMCO-791 monoclonal antibody to tumor cells was also compared with that obtained with a range of other murine monoclonal antibodies. These include antibodies recognizing CEA epitopes (B14B8, 194.2 and 161) and other anti-colon carcinoma antibodies. These test, summarized in Table VI, show that XMMCO-791 binds to 791T cells, whereas none of the other antibodies were reactive with this cell line. Both XMMCO-791 and the anti-CEA antibodies reacted with colon tumor cells (LS174T, C170, HT29) and weakly with bladder carcinoma T24.

4. Complement Dependent Cytotoxicity

The complement dependent cytotoxicity of monoclonal antibody XMMCO-791 for target cells derived from cultured tumor cell lines was assayed using a 2 hour, $^{51}$chromium ($^{51}$Cr) release assay (Price MR, et al., 1982).

Tumor cells ($5 \times 10^6$) were labeled with $^{51}$Cr. The cells were aliquoted into microtest plates that contained either medium or diluted monoclonal antibody preparations. As a source of complement, normal rabbit serum was added to each well. Following incubation at room temperature for 2 hours, the supernatants were collected and the percentage release of $^{51}$Cr was calculated for each test sample.

TABLE V

Indirect Membrane Immunofluorescence
Binding Activity of XMMCO-791
Monoclonal Antibody as Assessed
by Flow Cytofluorimetry

| Target Cell | Mean Fluorescence Units/Cell |
|---|---|
| Osteogenic Sarcoma | |
| 791T | 1733, 369, 709, 667 |
| 781T | 1899 |
| 788T | 338, 1572 |
| Colon Carcinoma | |
| HCT8 | 335 |
| HT29 | 111 |
| LS174T | 105, 173, 175 |
| HcLo | 322 |
| C146 | 351 |
| C168 | 184 |
| C170 | 302, 246 |
| Breast Carcinoma | |
| BT474.3 | 80 |
| Bladder Carcinoma | |
| T24 | 82, 95 |
| Ovarian Carcinoma | |
| PA1 | 18, 10 |

TABLE VI

Monoclonal Antibody Binding to Tumor Cells:
Indirect Flow Cytometry Assay

| Target Cell | Reagent | Fluorescence units/cell |
|---|---|---|
| Osteogenic Sarcoma | — | 30.0 |
| 791T | NMIg | 28.4 |
| | XMMCO-791 | 3380.0 |
| | SV2372 | 20.0 |
| | 19G415 | 45.9 |
| | B14B8 | 31.6 |
| | 194.2 | 35.2 |
| | FX13D4 | 65.7 |
| Colon Carcinoma | | |
| LS174T | — | 43.1 |
| | NMIg | 53.4 |
| | XMMCO-791 | 209.1 |
| | B14B8 | 1325.5 |
| | FX13D4 | 957.0 |
| | 194.2 | 1212.9 |
| C170 | — | 25.1 |
| | NMIg | 30.1 |

TABLE VI-continued

Monoclonal Antibody Binding to Tumor Cells: Indirect Flow Cytometry Assay

| Target Cell | Reagent | Fluorescence units/cell |
|---|---|---|
| | XMMCO-791 | 302.2 |
| | SV2372 | 27.9 |
| | 19G4.15 | 43.8 |
| | B14B8 | 59.2 |
| | 161 | 36.2 |
| | 45.2D9·C4 | 30.3 |
| HT29 | — | 41.4 |
| | NMIg | 47.0 |
| | XMMCO-791 | 111.2 |
| | 161 | 252.8 |
| | 194.2 | 47.6 |
| | FX13D4 | 56.0 |
| HCT8 | — | 36.9 |
| | NMIg | 31.1 |
| | XMMCO-791 | 335.2 |
| | 161 | 128.4 |
| | 194.2 | 37.3 |
| | FX13D4 | 926.4 |
| Bladder Carcinoma | — | 41.4 |
| T24 | NMIg | 47.0 |
| | XMMCO-791 | 82.0 |
| | 161 | 81.6 |
| | 194.2 | 44.6 |
| | FX13D4 | 60.0 |
| Breast Carcinoma | — | 70.4 |
| BT474.3 | NMIg | 76.5 |
| | XMMCO-791 | 196.5 |
| | B14B8 | 271.2 |
| | FXT3D4 | 87.9 |
| | 194.2 | 253.9 |
| | 161 | 281.4 |

Table VII summarizes tests on the complement mediated cytotoxicity of XMMCO-791 monoclonal antibody preparations. XMMCO-791 antibody was cytotoxic for osteogenic sarcoma derived cell lines 791T, 788T, 20S, and 278T, prostate carcinoma derived cell line EB33, and for HeLa cells, but not for ovarian carcinoma derived cell line PA1 or lung carcinoma A549 cells.

C. Antibody Binding to Human Malignant Cells and Tissues

1. Radioimmunoassay of XMMCO-791 Binding to Tumor Membranes

Monoclonal antibody XMMCO-791 binding to membrane preparations derived from surgically removed tumors was determined using a solid phase radioimmunoassay.

Tumor membrane preparations (ENM) were made by homogenizing fresh surgically removed tumor. Nuclei and cell debris were removed by centrifugation (600 g) and the ENM material sedimented at 105,000 g. ENM preparations attached to polyvinylchloride microtiter plates were used to assay antibody binding, this being detected by uptake of $^{125}$I-labeled rabbit anti-mouse IgG F(ab')$_2$ (Brown A., et al., 1983) (Table VIII). Positive tumor:nontumor ratios were obtained in 3.5 tumors.

2. Flow Cytometry

Binding of monoclonal antibody XMMCO-791 to malignant cells derived from primary and metastatic human tumors has been determined by flow cytometry. For this purpose, tumor cells were brought into suspension by collagenase treatment, and reacted with either XMMCO-791 or with control murine monoclonal antibodies. Cell bound immunoglobulin was then detected with FITC-conjugated rabbit anti-mouse Ig

TABLE VII

Complement Dependent Cytotoxicity of XMMCO-791 Monoclonal Antibody

| Cell Line | Cell Type | Percentage Cytotoxicity (Mean ± SD) Antibody at Protein Concentrations (μg/ml) | | |
|---|---|---|---|---|
| | | 125 | 25 | 5791T |
| 791T | Osteogenic sarcoma | 62 ± 2 (1 ± 1)* | 41 ± 2 | 12 ± 2 |
| 788T | Osteogenic sarcoma | 43 ± 1 (1 ± 1) | 25 ± 1 | 20 ± 2 |
| 278T | Osteogenic sarcoma | 50 ± 3 (1 ± 1) | 12 ± 1 | 4 ± 1 |
| 20S | Osteogenic sarcoma | 32 ± 2 (1 ± 1) | 1 ± 1 | 1 ± 1 |
| EB33 | Prostate carcinoma | 41 ± 6 (1 ± 1) | 4 ± 1 | 3 ± 1 |
| A549 | Lung carcinoma | 0 ± 1 (0 ± 0) | 0 ± 0 | 0 ± 0 |
| HeLa | Cervix carcinoma | 45 ± 4 (1 ± 1) | 28 ± 2 | 21 ± 2 |
| PA1 | Ovarian carcinoma | 0 ± 1 (1 ± 1) | 0 ± 0 | 0 ± 1 |

*Percentage cytotoxicity with heat inactivated complement.

TABLE VIII

Radioimmunoassay of Binding of XMMCO-791 to Colon Carcinoma and Normal Colon Membrane Preparations

| | XMMCO-791 antibody binding (cpm ± SD) to membrane preparations from | | |
|---|---|---|---|
| Patient | Colon Tumor (T) | Normal Colon (N) | T:N ratio |
| 109 | 842 ± 52 | 85 ± 41 | 9.9:1 |
| 147 | 620 ± 48 | 307 ± 31 | 2.0:1 |
| 162 | 318 ± 11 | 242 ± 34 | 1.3:1 |
| 167 | 2074 ± 71 | 286 ± 19 | 7.2:1 |
| 170 | 386 ± 54 | 360 ± 51 | 1.0:1 |

Membrane bound 791T/36 detected by $^{125}$I-labeled rabbit F(ab')$_2$ anti-mouse IgG.

and analyzed by flow cytometry. The analysis was restricted to the size range of malignant cells by appropriate forward angle scatter gating (Durrant L G, et al., 1986a).

TABLE VIII

Radioimmunoassay of Binding of XMMCO-791 to Colon Carcinoma and Normal Colon Membrane Preparations

| | XMMCO-791 antibody binding (cpm ± SD) to membrane preparations from | | |
|---|---|---|---|
| Patient | Colon Tumor (T) | Normal Colon (N) | T:N ratio |
| 109 | 842 ± 52 | 85 ± 41 | 9.9:1 |
| 147 | 620 ± 48 | 307 ± 31 | 2.0:1 |
| 162 | 318 ± 11 | 242 ± 34 | 1.3:1 |
| 167 | 2074 ± 71 | 286 ± 19 | 7.2:1 |
| 170 | 386 ± 54 | 360 ± 51 | 1.0:1 |

Membrane bound 791T/36 detected by $^{125}$I-labeled rabbit F(ab')$_2$ anti-mouse IgG.

XMMCO-791 antibody reaction with tumor cells derived from a primary colon carcinoma and from liver and lymph node metastases was tested. Significant binding of XXMCO-791 with tumor cells from both the primary and metastatic tumor was shown. For comparison, binding tests were carried out at the same time with two other murine monoclonal antibodies, C194 and C14 ¦ 1 ¦ 46; these MoAbs recognize CEA and Y hapten (Brown A., et al., 1983), respectively. Overall, the reaction with XMMCO-791 was comparable with that obtained with these antibodies.

The results of flow cytometry studies on binding of XMMCO-791 MoAbs to freshly disaggregated ovarian tumors are shown in Table VIIIa. The XMMCO-791

MoAb bound to the cell surface of all but one ovarian tumor. Intensity of staining was weak (MLF<100) in one tumor, moderate (MLFs 100–1000) in 8 and strong (MLF>1000) in one.

weight (72 kD) identical to that found on 791T cells, the original immunogen.

TABLE IX

Localization of $^{131}$I-Labeled XMMCO-791 Monoclonal Antibody in Primary Human Colorectal Carcinoma

| Clinical Data | Patient 1 | Patient 2 | Patient 3 |
|---|---|---|---|
| Tumor Type: | Rectal adenocarcinoma | Caecum adenocarcinoma | Sigmoid adenocarcinoma |
| Duke's Stage: | B | B | C |
| Degree of Differentation: | moderate | well | moderate |
| Tumor size (mm) | 30 × 20 | 35 × 35 | 85 × 60 |
| Patient Infused with: | $^{131}$I-XMMCO-791 + $^{125}$I-IgG$_{2b}$ | $^{131}$I-XMMCO-791 | $^{131}$I-XMMCO-791 |
| Period Between Antibody Infusion and Tumor resection(days): | 1 | 3 | 3 |
| Distribution of radioactivity of dose of $^{131}$I-XXMCO-791 per g of tumor tissue: | 0.008 | 0.003 | 0.004 |
| Tumor:Normal Tissue Ratio: | 3.3:1($^{131}$I) 1.2:1($^{125}$I) | 2.0:1($^{131}$I) | 1.8:1($^{131}$I) |
| Radioactivity ($^{131}$I) Recovered in Fibrous Material from tumor tissue: | 87 | 83 | 74 |

D. Antibody Binding to Normal Human Cells
  1. Reactivity of XMMCO-791 Monoclonal Antibody TABLE VIIIa Flow Cytometric Analysis of Binding of 791T/36 to the Cell Surface of Freshly Disaggregated Ovarian Tumors Indirect Immunofluorescence on Ovarian Tumor Cells (Mean Linear Fluorescence, MLF):

| | Ov1 | Ov2 | Ov3 | Ov4 | Ov5 | Ov6 | Ov9 | Ov9 | Ov10 (met)[1] | Ov11 | Ov12 |
|---|---|---|---|---|---|---|---|---|---|---|---|
| Antibody 791T/36 | 138 | 61 | 105 | 138 | 135 | 105 | 249 | 456 | 94 | 155 | 1808 |
| Normal mouse IgG | 36 | 54 | 20 | 21 | 41 | 20 | 51 | 58 | 17 | 51 | 133 |

[1]Peritoneal metastases of primary tumor Ov9

3. Characterization of XMMCO-791 Binding Antigen in Human Primary Colon Carcinoma Tumors As will be described later, studies carried out at University of Nottingham, U.K., with appropriate regulatory approval, demonstrated that the MoAb XMMCO-791, when injected in vivo, localizes in primary and metastatic human colon cancers. Thus, studies were carried out to identify the antigen to which the antibody is bound in vivo.

Briefly, 200 μg $^{131}$I-XMMCO-791 containing 2 mCi $^{131}$I was injected into patients with primary colon carcinomas, and 1–6 days later normal colon tissue and colon tumors were resected. Tissues were homogenized and the fibrous material was extracted. The extract was then mixed with Affi Gel 10 (BioRad Laboratories, Richmond, CA), to which affinity purified goat anti-mouse IgG antibody had been linked. The pellets contained the bound $^{131}$I-labeled material from the tissue extract. This was reacted with $^{125}$I to label tissue protein.

After washing, the Affi Gel pellet was treated with sodium isothiocyanate to release bound $^{131}$I-labeled XMMCO-791 antibody, either free or complexed with antigen.

After purification by gel chromatography, the extract was incubated with Sepharose-Protein A to isolate Ig containing material. These products were removed from the gel and SDS-Polyacrylamide-Gel-Electrophoresis (SDS-PAGE) was carried out. The results are summarized in Table IX.

The apparent molecular weights of two of the bands at 60 kD and 25 kD corresponded to those for heavy and light chains of the XMMCO-791 IgG2b antibody. The third band at 72 kD corresponded to that of the XMMCO-791-defined antigen isolated from 791T cells. The conclusion from the studies is that following infusion of XMMCO-791 antibody into colorectal carcinoma patients, the antibody localizes within the tumor by binding to tumor-associated antigen of molecular weight (72 kD) identical to that found on 791T cells, the original immunogen.

with Human Peripheral Blood Mononuclear Cells (PBMC) Analyzed by Flow Cytometry a. Lymphocytes Using direct and indirect immunofluorescence assays, XMMCO-791 antibody was shown to react strongly with phytohemagglutin (PHA) (Sigma) stimulated lymphoctyes from peripheral blood and negligibly with resting lymphocytes. Maximum binding was observed after 3 days culture with PHA (5 μg/ml), coinciding with maximum DNA synthesis. Comparable results were obtained using concanavalin A (Con A) (10 μg/ml) as mitogen (Table X).

XMMCO-791 antibody precipitated a protein of apparent molecular weight of 72,000 from cells cultured 3 days with PHA. No other bands at 72,000 were precipitated from other cultures of PBMC and no 72,000 molecular weight material was precipitated from PHA-stimulated PBMC using normal mouse immunoglobulin, rather than XMMCO-791 antibody.

b. Blood Granulocytes

Binding of XMMCO-791 to peripheral blood granulocytes has been determined using an indirect flow cytometry assay.

Table XI summarizes a series of tests of 9 lots of XMMCO-791 before and after ultracentrifugation with blood granulocytes from 2 donors. The binding of XMMCO-791 to granulocytes was compared with that of supernatant made by the parental myeloma line, P3NSI/1-Ag4-1. 8/9 lots showed negative binding. One lot showed moderate binding which became negative after centrifugation.

TABLE X

Binding of FITC-labeled XMMCO-791 Antibody to Mitogen-Stimulated PBMN Cells as Assessed by Quantitative Flow Cytofluorimetry

| Cell Subpopulation Analyzed | Percentage of cells in subpopulation analyzed (mean ± SD) | Number of FITC-XMMCO-791 antibody molecules binding/cell ($\times 10^{-5}$) (mean ± SD) |
|---|---|---|
| Small lymphocytes from non-stimulated PBMN cell preparations | 93.4 + 3.8 (n = 18) | <0.1 (n = 18) |
| Lymphoblasts from PBMN cell preparations cultured with PHA for 3 days | 45.5 ± 22.2 (n = 17) | 1.1 ± 0.4 (n = 17) |
| Lymphoblasts from PBMN cell preparations cultured with Con A for 3 days | 60.6 ± 12.0 (n = 6) | 0.9 ± 0.5 (n = 6) |

The number of determinations (n) is given in parenthesis

TABLE XI

Monoclonal Antibody XMMCO-791 Binding to Blood Granulocytes. Indirect FACS Analysis Before and After Centrifugation

| | | Mean Fluorescence Intensity/Cell | | | |
|---|---|---|---|---|---|
| | | Donor 1 | | Donor 2 | |
| No. | Sample | Before | After* | Before | After |
| 1 | 3929 | 83.9 | 27.7 | 67.0 | 28.6 |
| 2 | 4110 | 24.2 | 24.7 | 21.4 | 25.4 |
| 3 | 3619 | 34.8 | 35.8 | 34.9 | 32.1 |
| 4 | 4086 | 25.0 | 22.5 | 31.1 | 29.1 |
| 5 | 4056 | 24.1 | 25.1 | 25.4 | 31.1 |
| 6 | 3984 | 27.6 | 25.1 | 45.2 | 32.3 |
| 7 | 50108 | 25.1 | 22.7 | 28.9 | 28.6 |
| 8 | 4110 | — | — | 28.6 | 28.5 |
| 9 | P3NS1 | 19.8 | | 19.2 | |

*Ultracentrifuged 105,000 g/60 minutes

E. Binding to Other Normal Human Tissues Measured By Immunoperoxides

XMMCO-791 was extensively evaluated for cross-reactivity with normal tissues using the indirect immunoperoxidase conjugate technique. As a control, tissues were simultaneously tested with a purified murine MoAb in the same concentration. The control immunoglobulins used for these purposes were an IgG2 mouse myeloma protein (UPC 10, Litton Bionetics, Kensington, MD) or a MoAb with reactivity to sheep red blood cells (SRBC).

Fresh tissue slices (2-3 mm thickness and up to 2.0 cm in width) was generously coated with Optimal Cutting Temperature Compound (OCT), (Ames Co., Elkhar, Ind.) and wrapped in aluminum foil. The specimen was "snap" frozen in liquid nitrogen-cooled isopentane (2-methylbutane, VWR, Norwald, CA) at controlled temperature ($-120°$ to $-150°$ C.) for 10-15 seconds. The tissue was kept frozen for long-term storage at $-70°$ C., or for short-term storage at $-20°$ C., in a tightly sealed container to prevent evaporation and drying of tissues. Frozen tissues were allowed to equilibrate slowly overnight by placing in a $-35°$ C. cryostat prior to cutting the frozen sections. Cut sections were dried overnight at room temperature prior to staining.

A circle was etched on each slide around the tissue using a diamond pencil. Slides were then fixed in acetone for 1 minute, followed by a 10 minute PBS wash. Excess fluid was removed and the primary antibody applied for one hour while making sure that the tissue was covered and not allowed to dry out, followed by a 10 minute PBS wash.

Excess fluid was removed and peroxidase-conjugated goat anti-mouse IgG (Tago/product code 6450) (diluted 1:10 in PBS) applied for 30 minutes, followed by a 10 minute PBS wash.

The slides were developed in aminoethylcarbazole (AEC), (0.5 ml AEC stock 120 mg AEC in 15 ml dimethylformamide), 9.5 ml acetate buffer (79 ml of 0.1M sodium acetate, 21 ml of 0.1N acetic acid), and 0.05 ml 3% $H_2O_2$) for 5 minutes, followed by a 5 minute $H_2O$ wash. The slides were then counterstained with fresh Mayer's Hemtoxylin for 5 minutes, followed by a 5 minute wash in running tap water and coverslipped with glycerine mounting media. The following is a summary of the results:

Throughout the study, connective tissue (ground substance) was positive.

The vascular endothelium of capillaries and venules in varying tissues were mildly positive but not all venules were positive in any tissue.

Lung tissue from 2/4 autopsy specimens showed some reactivity with about 10% of the alveolar epithelium/macrophages in each of the two specimens; most reactivity was in macrophages.

Kidney tissue showed faint glomeruli staining in 10% of the sample in 1/4 autopsy specimens.

Skin showed staining in the lumen of ducts in 2/4 autopsy specimens.

Colon showed slight staining of glandular epithelium in both colon specimens tested.

Fetal tissue showed some staining in alveolar and bronchial epithelium of the lung; some positive tubule lumen in the kidney.

There was no staining (except for connective tissue and venules) in:

| | | |
|---|---|---|
| Thyroid | Liver | Heart |
| Breast | Adrenal | Muscle |
| Spinal cord | Nerve | Thymus |
| Testes | Diaphragm | Uterus |
| Esophagus | Pancreas | Aorta |
| Spleen | Brain | |

Note:
Granulocytes will appear positive in both control and test tissue because of endogenous perxidase.

F. Identification of the Cell Antigen Binding XMMCO-791

1. Osteogenic Sarcoma Derived 791T Cells 791T cells were surface-labeled with $^{125}I$ by lactoperoxidase catalyzed radioiodination and lysed. A lysate containing $^{125}I$-labeled membrane protein was obtained. Sodium dodecyl sulfate (SDS) and XMMCO-791 MoAb were added to aliquots of this cell lysate, followed by Sepharose-Protein A beads. The beads were washed and final pellets were suspended in reducing gel sample buffer. After incubation, supernatants were anlayzed by polyacrylamide gel electrophoresis. Gels were stained for protein with Coomassie blue and, after drying, autoradiographed.

The antigen precipitated by the MoAb XMMCO-791 from detergent lysates of $^{125}I$-labeled 791T cells migrated in SDS-PAGE slab gels with an apparent molecular weight of 72,000. Both reduced and non-reduced samples gave equivalent results, indicating that the antigen is a monomeric cell surface protein. The relatively broad band suggests that the antigen may be glycosylated, with microheterogeneity in the saccharide residues producing the wide band. When immunoprecipitates were treated with neuraminidase, the apparent molecular weight was reduced to 55,000, indicative of extensive glycosylation. Since microheterogeneity in the band of precipitated material was lost following neuraminidase treatment, this indicated that microheterogeneity was attributable to variations in sialic acid content.

That the gp72 antigen is glycosylated was confirmed by labeling growing tumor cells with $^3$H glucosamine and again precipitating a 72,000 molecular weight antigen which was radiolabeled.

2. Other Human Tumor Cell Lines

Seven cell lines known to express the antigen recognized by XMMCO-791 were selected. Four of these were osteogenic sarcomas, two were colon carcinomas, and one was a prostate carcinoma cell line. Negative controls included lung carcinoma, breast carcinoma, and malignant melanoma cell lines.

These 10 human tumor cell lines were surface-labeled with $^{125}$I, lysed with detergent and subjected to radioimmunoprecipitation using either the XMMCO-791 monoclonal antibody or normal mouse immunoglobulin. The immune precipitates were isolated using Sepharose-Protein A and analyzed by SDS-PAGE and autoradiography. The XMMCO-791 antibody precipitated a protein from 791T cells of apparent molecular weight of 72,000 in accordance with previous findings. Five other cell lines contained protein material of apparent molecular weight of about 72,000 that was also precipitated by the XMMCO-791 antibody. Colon carcinoma cell line HT29 gave anomalous results, since despite repeated testing, no protein was precipitable with the XMMCO-791 antibody. The cell lines A549, B55, and RPMI 1566, which are unreactive with the XMMCO-791 antibody, failed to express a 72,000 dalton antigen in these immunoprecipitation studies.

It is evident from these studies that the precipitates from the other cell lines which bound XMMCO-791 MoAb were not identical to that from the 791T cell line, although proteins of 72,000 daltons were detected in each case. These differences may be due to antigen heterogeneity (characteristic of carbohydrate-rich glycoprotein antigens) and/or variations in the specific activity of the antigens with respect to radiolabeling. The cell line EB33 clearly showed two distinguishable components of 72,000 and 55,000 daltons that were precipitated by the XMMCO-791 antibody.

a. Effect of Neuraminidase Treatment

Neuraminidase reduced the apparent molecular weight of the precipitate antigens in five of the six cell lines tested to a uniform value of 55,000 daltons. These results indicate, first, that the precipitated labeled protein antigens are glycosylated and, second, that their molecular heterogeneity is attributable to differences in sialic acid content. The protein precipitated from the colon carcinoma cell line HcLo was apparently not affected by treatment with neuraminidase.

b. Effect of Chymotrypsin Treatment

Radiolabeled immune precipitates were treated with chymotrypsin and analyzed by SDS-PAGE and autoradiography to compare the XMMCO-791 defined antigens with respect to their susceptibility to proteolysis. The XMMCO-791-defined antigen proved to be very resistant to degradation, the major chymotryptic product in each case being a polypeptide with an apparent molecular weight of 47,000. This would indicate that each of the antigens immunoprecipitated with the XMMCO-791 antibody have at least one chymotryptic site in common. The major 47,000 molecular weight polypeptides from the six tumor cell lines examined did not display the molecular heterogeneity associated with the non-enzyme-treated XMMCO-791-defined antigens. This would imply that the portion(s) of the molecule exhibiting a variable content of sialic acids was (were) removed by proteolysis with chymotrypsin. It may be noted that the antigen from the cell line HcLo was not anomalous with respect to its susceptibility to chymotryspin. This contrasts with its apparent resistance to neuraminidase since the major polypeptide generated was of 47,000 dalton molecular weight.

3. Effect of Papain on the gp72 antigen

Previous studies have demonstrated that 791T cells treated with papain no longer bind XMMCO-791 antibody, indicative of the degradation or release of XMMCO-791-defined antigen. To define the action of papain more precisely, 791T cells were radiolabeled with $^{125}$I and treated with papain. After centrifugation, the solubilized extract of cell membrane proteins and glycoproteins was subjected to radioimmunoprecipitation using XMMCO-791 antibody and Sepharose-Protein A, and the immune precipitates were analyzed by SDS-PAGE and autoradiography. The results indicate that papain digestion released an antigenically active protein fragment of apparent molecular weight of 53,000. Neuraminidase treatment of the immune precipitate prepared as above effected a further reduction in apparent molecular weight to 50,000, indicating that this papain fragment was glycosylated and carried sialic acid residues. 4. Purification of the $^{125}$I Labeled gp72 Antigen To develop a purification procedure for the gp72 antigen, 791T cells were surface labeled with $^{125}$I and lysed with detergent. After centrifugation and dialysis, the soluble extract was fractionated by immunoadsorbent chromatography by passage through two non-specific adsorbent columns (Sepharose 4B and Affi Gel 10-linked mouse IgG) and a specific immunoadsorbent column (Affi Gel 10-linked XMMCO-791 monoclonal antibody) connected in series. The XMMCO-791 antibody immunoadsorbent was eluted and rechromatographed.

The purified antigen consisted of a major band at 72,000 daltons. There was also a minor band of slightly lower molecular weight; it may be due to carbohydrate heterogeneity.

5. Binding of $^{125}$I-Labeled gp72 to Lectins

The binding of $^{125}$I-labeled XMMCO-791-defined antigen to lectins was investigated. After incubation of aliquots of the antigen preparation ($1 \times 10^4$ cpm) with Sepharose-wheat germ agglutinin (WGA), Sepharose-Con A and Sepharose-lentil lectin, bound glycoproteins were eluted and analyzed by SDS-PAGE and autoradiography. The material eluted from Sepharose-WGA migrated with an apparent molecular weight of 72,000, indicating the presence of N-acetyl-glucosamine in this glycoprotein. Equivalent material was also bound to Sepharose-Con A, but no bands were seen with eluates from Sepharose-lentil lectin or Sepharose alone. Of the radioactivity recovered in the eluates from these columns, 69% was present in the fraction bound and eluted from Sepharose-WGA, 49% was bound and eluted from Sepharose-Con A, 23% from Sepharose-lentil lectin and 9% from Sepharose alone.

6. Conclusions

XMMCO-791 MoAb reacts with the osteogenic sarcoma cell line 791T used for initial immunization. The XMMCO-791-defined epitope on this cell line is expressed on a protein of apparent molecular weight 72,000. The MoAb also reacts with cell lines other than this one. An investigation was performed to determine whether the epitope occurred on similar molecules on these other cell lines. It was concluded that molecules expressing this epitope do exist on other tumor cell lines. These molecules are glycoproteins that have different molecular weights. This difference is attributable to varying degrees of sialyation. There are no apparent differences in the polypeptide "backbone" of these antigenic molecules. Radiolabeled immunoprecipitates, prepared with the XMMCO-791 antibody, from three osteogenic sarcoma cell lines (2 OS, 788T, and 278T), the prostate carcinoma EB33 and the colon carcinoma HcLo each contained a protein with a molecular weight of 72,000 as the major constituent and, in some cases, material of lower weight. By neuraminidase treatment of the immune precipitates, this heterogeneity was shown to be due to variations in sialic acid content of the antigens since; in five of the six cell lines tested, such treatment produced homogeneous material of apparent molecular weight 55,000. Chymotrypsin treatment of the immune precipitates produced in each instance a major polypeptide of molecular weight 47,000 which displayed no microheterogeneity. Immunoadsorbent-purified antigen from 791T cells was shown to bind strongly to Sepharose-concanavalin A, confirming the glycoprotein nature of this antigen. These results are summarized in Table XII.

1. Complement Dependent Cytotoxicity

Complement dependent cytotoxicity of monoclonal antibody XMMCO-791 was assayed in a 2 hour $^{51}$Chromium release assay. It was found that only rabbit serum served as an effective complement source for lysis of target cells (Table XIII).

2. Antibody Dependent Cellular Cytotoxicity (ADCC)

Experiments were carried out to determine whether XMMCO-791 mediated ADCC reactions (Flannery et al., *Eur. J. Cancer Clin. Oncol.* (1984) 20:791-98). $^{51}$Cr-labeled target cells (791T, and the human erythroleukemic cell line K562) were incubated with appropriate dilutions of antibody and aliquoted into microtiter wells. Appropriate numbers of human mononuclear cells were added.

XMMCO-791 is not able to mediate ADCC against either 791T cells or K562 cells at concentrations of antibody ranging from 10 to 0.1 μg/ml and with effector:target cell ratios ranging from 0.8:1 to 3:1.

3. In Vivo Inhibition of Tumor Growth

The effect of XMMCO-791 monoclonal antibody alone on the in vivo growth of human tumors was assessed using xenograft systems. 791T cells were implanted subcutaneously into mice immunodeprived by thymectomy and whole body irradiation. Mice were treated with XMMCO-791 antibody starting 1 to 5 days after 791T implantation and were treated at intervals thereafter.

Three injections of either 40 μg or 80 μg did not modify growth of 791T xenografts. In further tests, doses of up to 181 μg/kg body weight (given in 9 divided doses) have not suppressed growth of 791T xeno-

TABLE XII
REACTIVITY OF THE MONOCLONAL ANTIBODY XMMCO-791 WITH CULTURED HUMAN CELLS

| Target Cell | Antibody reactivity viable target cells | | Apparent molecular weight ($\times 10^{-3}$) of antigen (SDS-PAGE)[3] | |
|---|---|---|---|---|
| | Cell binding activity[1] | Antibody molecules bound per cell ($\times 10^4$)[2] | Before neuraminidase | After neuraminidase |
| Osteogenic Sarcomas: | | | | |
| 791T | +++ | 220 | 72 | 55 |
| 788T | +++ | 160 | 72 | 55 |
| 278T | ++ | 51 | 72 | 55 |
| 20S | + | 53 | 72 | 55 |
| Carcinomas: | | | | |
| HcLo (colon) | +++ | ND | 72 | 72 |
| HT29 (colon) | ++ | ND | No precipitate | NR |
| EB33 (prostate) | +++ | 35 | 72;55 | 55 |
| A549 (lung) | --- | ND | No precipitate | NR |
| B55 (breast) | --- | ND | No precipitate | NR |
| Melanoma: | | | | |
| RPM1 1566 | --- | <2 | No precipitate | NR |

[1]Cell-binding of XMMCO-791 antibody was determined using the indirect $^{125}$I-Protein A binding assay (Embleton MJ, et al, 1981). +++ represents binding ratios >10. ++ represents binding ratios of 5-10. + represents binding ratios of 2-5 and --- represents binding ratios <2 where binding ratio = (mean cpm bound to cells treated with XMMCO-791 antibody)/(mean cpm bound to cells treated with P3NS1 spent medium).
[2]Quantitative binding of $^{125}$I-labeled XMMCO-791 antibody determined by Price MR, et al. (1982a).
[3](Price MR, et al, 1983b)
ND, not determined
NR, not relevant

G. Biological Properties of XMMCO-791 grafts.

TABLE XIII
Complement-Dependent Cytotoxicity of Anti-791T Monoclonal Antibody XMMCO-791 Screen of Complement Sources

| | % Cytotoxicity Against | | | | | |
|---|---|---|---|---|---|---|
| | 791T/Cells Treated With | | | | PHA-Blasts Treated With | |
| Serum Source of Complement* | Medium | XMMCO-791 | Anti-791T/48+ | W6/32++ | Medium | W6/32++ |
| Rabbit | −0.3 ± 0.3 | 53.8 ± 4.7 | 29.1 ± 2.8 | 46.1 ± 5.3 | 8.4 ± 0.8 | 62.3 ± 3.5 |

TABLE XIII-continued

Complement-Dependent Cytotoxicity of Anti-791T Monoclonal Antibody XMMCO-791
Screen of Complement Sources

| Serum Source of Complement* | % Cytotoxicity Against | | | | | |
|---|---|---|---|---|---|---|
| | 791T/Cells Treated With | | | | PHA-Blasts Treated With | |
| | Medium | XMMCO-791 | Anti-791T/48+ | W6/32++ | Medium | W6/32++ |
| Mouse | (−0.2 ± 0.1) | (0.7 ± 0.5) | (0.4 ± 0.6) | (0.9 ± 0.5) | (−0.4 ± 0.6) | (0.0 ± 0.2) |
| | 0.3 ± 0.2 | 0.0 ± 0.2 | 0.0 ± 0.1 | 0.0 ± 0.3 | 0.2 ± 0.7 | 0.4 ± 1.2 |
| Human Pool | (0.2 ± 0.3) | (−0.1 ± 0.2) | (0.3 ± 0.2) | (0.1 ± 0.1) | (−0.8 ± 0.7) | (0.3 ± 0.4) |
| | 0.0 ± 0.2 | 0.1 ± 0.1 | 0.1 ± 0.1 | −0.3 ± 0.2 | 2.1 ± 0.6 | 76.3 ± 0.9 |
| Human (1) | (−0.1 ± 0.2) | (0.5 ± 0.3) | (0.3 ± 0.2) | (−0.3 ± 0.2) | (−0.3 ± 1.0) | (0.6 ± 0.9) |
| | 0.0 ± 0.4 | 0.1 ± 0.2 | 0.4 ± 0.5 | 0.0 ± 0.4 | 0.6 ± 0.7 | 67.6 ± 5.5 |
| Human (2) | (0.0 ± 0.3) | (0.4 ± 0.3) | (0.7 ± 0.6) | (0.1 ± 0.1) | (0.4 ± 0.3) | (0.6 ± 0.6) |
| | 0.2 ± 0.5 | 0.2 ± 0.1 | 0.3 ± 0.2 | −0.5 ± 0.2 | 1.0 ± 1.1 | 66.4 ± 7.2 |
| Human (3) | (0.3 ± 0.2) | (−0.2 ± 0.3) | (0.1 ± 0.4) | (−0.6 ± 0.3) | (−0.3 ± 0.7) | (1.2 ± 1.2) |
| | −0.3 ± 0.1 | 0.1 ± 0.3 | 0.4 ± 0.2 | −0.4 ± 0.3 | 1.0 ± 1.0 | 74.8 ± 4.8 |
| Guinea-pig | (−0.1 ± 0.2) | (0.6 ± 0.2) | (1.0 ± 0.3) | (−0.8 ± 0.2) | (−0.6 ± 0.9) | (0.7 ± 1.3) |
| | 0.3 ± 0.5 | 0.1 ± 0.3 | 0.2 ± 0.2 | 0.5 ± 0.2 | 1.1 ± 0.4 | 40.7 ± 4.7 |
| | (0.0 ± 0.5) | (−0.1 ± 0.2) | (0.1 ± 0.2) | (0.5 ± 0.1) | (−0.1 ± 0.3) | (0.1 ± 0.7) |

*Final dilution of serum — 1/5.
+ XMMCO-791 and anti-791T/48 monoclonal antibodies were tested at a final concentration of 125 μ/ml.
++ W6/32 monoclonal antibody was tested at a final dilution of 1/500 of the serum/ascites fluid.
Figures in parenthesis represent % cytotoxicities determined in the presence of heat-inactivated complement.

H. Conjugation of XMMCO-791 With Ricin Toxin A Chain (RTA)

The conjugation of RTA to an immunoglobulin has been thoroughly described in U.S. Pat. No. 4,590,071, the disclosures of which are hereby incorporated by reference. U.S. Pat. No. 4,590,071 fully discloses the technique for RTA purification employing anti-ricin B chain antibodies as well as the conjugation methodology.

I. Characterization of the Immunotoxin

XMMCO-791-RTA was characterized biochemically by SDS-PAGE and functionally by flow cytometry measurement of binding to colorectal carcinoma derived C170 cells and to control MOLT-4 cells (A.T.C.C. Accession No. CRL 1582). It was also characterized by assays that either measured its ability to inhibit protein synthesis in a cell-free system or to kill 791T cells.

In order to determine lot to lot variation, three replicate research lots of immunotoxin were made from the same lot of XMMCO-791 and the same lot of RTA. The conjugations and purifications were done separately but simultaneously. These lots, 51016 A, B, and C, are compared within each section to show lot to lot variation and preliminary data on stability. They have been analyzed by SDS-PAGE, flow cytometry, reticulocyte lysate and whole cell cytotoxicity assays at various times after preparation. The data indicate that the lot to lot variation is minimal, and that the immunotoxins are stable for a least three months.

Results from the assays on a production lot of immunotoxin are also presented in each section. Research lots are prepared in small quantities, whereas production lots are prepared in larger batches under aseptic clean room conditions. The conjugation procedure is the same, but scale up production often produces an increased degree of conjugation. This can be decreased by adjustment of the N-succinimidyl 3-(2-pyridyldithio) propionate (SPDP) ratio. All lots were very similar, both functionally and biochemically.

1. SDS-PAGE Analysis
   a. The Assay

SDS-PAGE analysis of immunotoxins run under nonreducing conditions provides information about the amount of free (unconjugated) antibody remaining in the preparation, the mean RTA/MoAb ratio, the presence of unbound RTA in the preparation, and the number of molecular species present. Two gel analyses are run on each immunotoxin preparation. A 10% nonreduced SDS-PAGE was run to determine the presence of free RTA, producing poor discrimination between the free antibody and the RTA-MoAb conjugates that tend to cluster near the top of the gel. However, it allows excellent definition of any free RTA, which when present is seen as two bands at 30 kD and 33 kD. Free RTA generally constitutes less than 5% if the total protein in freshly prepared conjugate and RTA bands are rarely seen.

A nonreduced SDS-PAGE was run in a 3 −7.5% gradient. This allows accurate detection of the molecular species of conjugate present. Free antibody appears as a band at approximately 160 kD, and immunotoxins with 1, 2, 3 or more RTAs per MoAb appear at appropriate locations reflecting their increased molecular weight.

b. Results

SDS-PAGE analyses were performed on the three replicate research lots of XMMCO-791-RTA and on one of the production lots within two weeks of immunotoxin preparation. The amount of free antibody is similar within the replicate lots, ranging from 1 to 2%. This is typical of free antibody values seen in other research lots. Table XIV summarizes the biochemical characteristics of the replicate and production lots. The RTA to IgG ratio ranged from 3.0 to 3.4 on the replicate lots. Molecular species corresponding to free MoAb or 1-6 RTA/MoAb were seen; this was similar for all research lots. By nonreduced 10% SDS-PAGE, about 5% free RTA was detected.

TABLE XIV

| | Percent of Components in Small or Large Lots of Immunotoxin | | | |
|---|---|---|---|---|
| | 51203[1] | 51016A[2] | 51016B[2] | 51016C[2] |
| Free RTA | 0 | 5.3% | 5.6% | 4.4% |
| Free MoAB | 0 | 1.1% | 2.1% | 2.2% |
| Monomer | 0 | 12 | 10 | 10 |
| Dimer | 4% | 25 | 21 | 10 |
| Trimer | 18% | 30 | 27 | 29 |
| Tetramer | 32% | 21 | 23 | 26 |
| Pentamer | 46% | 8% | 12 | 16 |
| Hexamer | — | 3% | 5 | 7 |

TABLE XIV-continued

| | Percent of Components in Small or Large Lots of Immunotoxin | | | |
|---|---|---|---|---|
| | 51203[1] | 51016A[2] | 51016B[2] | 51016C[2] |
| RTA:MoAb ratio | 4.2 | 3.0 | 3.2 | 3.4 |

[1]Production lot, yield 1000 mg
[2]Replicate lots, yield approximately 20 mg

The production lot, 51203, was used for stability testing, and the results of these tests at one and two months are shown in Table XV, indicating that the product is stable. Four molecular species were detected on nonreduced gradient gels, corresponding to dimers, trimers, tetramers and pentamers. There was no free antibody and no band corresponding to monomers. Nonreduced 10% gels showed that minimal free RTA was present.

c. Summary

Both research and production lots showed little free RTA when freshly prepared. The research lots had up to 1–3% free antibody and molecular species corresponding to 1–6 RTA/MoAb, whereas the production lot had no detectable free antibody and no detectable monomers. Molecular species of up to five RTA/MoAb were present in the production lot. Little deterioration was noted over 3 months.

2. Flow Cytometry Studies, XMMCO-791-RTA Binding to C170 Cell Line a. The Assay

The competitive inhibition assay, by which flow cytometry is utilized to determine binding of unlabeled XMMCO-791 to C170 colon carcinoma cells, is known to those skilled in the art. This assay is particularly well-suited to assess retention of antibody binding in drug antibody conjugates such as immunotoxins because it measures the ability of unlabeled antibody to specifically compete with FITC-labeled homologous antibody for antigen binding sites.

TABLE V-6

| | Change in Composition of Replicate Lots of XMMCO-791-RTA With Time | | | | | |
|---|---|---|---|---|---|---|
| | 51016 A | | 51016 B | | 51016 C | |
| | Initial | 3 mo | Initial | 3 mo | Initial | 3 mo |
| Free RTA | 5.3 | 2.9 | 5.6 | 3.7 | 4.4 | 2.6 |
| Free MoAB | 1.1 | 4.3 | 2.1 | 3.3 | 2.2 | 1.8 |
| Monomer | 12 | 18 | 10 | 15 | 10 | 13 |
| Dimer | 25 | 28 | 21 | 26 | 10 | 27 |
| Trimer | 30 | 27 | 27 | 31 | 29 | 27 |
| Tetramer | 21 | 23 | 23 | 25 | 26 | 31 |
| Pentamer | 8 | 0 | 12 | 0 | 16 | 0 |
| Hexamers | 3 | 0 | 5 | 0 | 7 | 0 |
| RTA:MoAb Ratio | 3.0 | 2.5 | 3.2 | 2.6 | 3.4 | 2.7 |

The reference curve was generated by mixing unlabeled XMMCO-791 standard with FITC-XMMCO-791 and reacting it with C170 cells. This was the positive control. Negative controls included an unlabeled antibody that does not bind to C170 and thus cannot compete. The slope of this line is zero.

The immunotoxin was evaluated by comparing it with its "parent lot"—the MoAb from the same lot used for RTA conjugation. Thus, two sets of mixtures were prepared, the first being a mixture of MoAb from the immunotoxin parent lot with the standard FITC-MoAb and the second, a mixture of the immunotoxin with the FITC-MoAb. When the mixtures were added to C170 cells and assessed for fluorescence intensity by flow cytometry, two lines were generated. Comparison of the slope of the line generated by the parent MoAb with that of the immunotoxin describes the degree of activity retained by the immunotoxin. Since the assay is highly concentration dependent, it was necessary to correct the concentration of the immunotoxin so that is was expressed in terms of antibody concentration instead of immunotoxin concentration.

b. Results

Both the replicate lots had RTA to MoAb ratios of 3–3.4 RTA:MoAb; the more highly conjugated production lot had 4.2. The lots tested for binding at various times after conjugation. The results are shown in Table XVI, and are expressed either as amount of unlabeled antibody necessary to decrease fluorescence by 50% ($IF_{50}$) or as percent decrease in line slope. By the latter parameter, it can be seen that there was little difference in the replicate lots, all of which bound about 80% of their parent lot. Moreover, there was little noticeable deterioration, and testing three months after production still revealed binding that was greater than 80% of the parent lot. Table XVI also shows the percent binding of the production lot 51203, which had a higher RTA:MoAb ratio than the smaller lots and bound 48% of the parent lot. There was no decrease in binding two months after conjugation.

c. Summary

Replicate lots made under the same conditions showed uniform binding and little loss of activity compared to unconjugated parent lot. There was no apparent decrease in binding over a three-month period. This demonstrates that RTA:MoAb ratios of 3:1 produce little loss in activity.

The first production lot had an RTA:MoAb ratio of 4.2:1 and decreased binding to about 50% of the unconjugated parent lot. Although this had little effect on either the whole cell cytotoxicity assay, the xenograft therapy trials, or the toxicity, we feel that this represents the upper limit of desirable conjugation. In spite of the higher degree of conjugation, there was no apparent decrease in binding over a two-month period.

TABLE XVI

| Binding by Flow Cytometry of Lots of XMMCO-791-RTA Assayed at Various Times After Conjugation | | | |
|---|---|---|---|
| Lot | Time After Conjugation | $IF_{50}$ test / $IF_{50}$ Parent | Ratio of Test Slope To Parent Slope |
| 51016A | 2 Weeks | — | |
| | 1 Month | 77% | 79.8% |
| | 2 Month | 82% | 89.1% |
| | 3 Month | 79% | 83.9% |
| B | 2 Weeks | — | |
| | 1 Month | 79% | 81.9% |
| | 2 Month | 88% | 95.3% |
| | 3 Month | 80% | 88.3% |
| C | 2 Weeks | — | |
| | 1 Month | 80% | 84.0% |
| | 2 Month | 81% | 86.3% |
| | 3 Month | 77% | 83.0% |
| 51203 | 2 Weeks | 45% | 47.7% |
| | 1 Month | 50% | 52.2% |

3. Reticulocyte Lysate Assay a. The Assay

This assay measured the ability of XMMCO-791-RTA to inhibit protein synthesis in a cell free system, and compared it with the inhibition producted by free RTA. Although both bound and free RTA should theoretically produce the same amount of inhibition, there is usually a slight loss of activity in the conjugate when the two compounds are compared on the basis of RTA molarity.

Rabbit reticulocyte lysate is prepared by lysing rabbit reticulocytes (precursor red blood cells) in water. A nutrient solution is prepared consisting of standard preparations of all amino acids (except leucine), $^{14}C$-leucine, salts, EDTA, hemin (enzyme co-factor), and creatine phosphokinase (the enzyme which catalyzes translation). This solution contains all materials necessary for protein synthesis.

Dilutions of RTA or RTA-containing products were added to types containing the nutrient solution and the lysate. The incorporation of $^{14}C$-leucine into protein by the lysate was measured to determine the degree of inhibition of protein synthesis. Results are expressed as a percentage compared to non-RTA containing tubes (100% reference).

Values are expressed as gm/ml producing 50% inhibition of protein synthesis ($IC_{50}$). The assay may vary by ±2.5 fold in replicate analysis.

b. Results

Table XVII shows assays on the three replicate immunotoxin lots and one production lot. When plotted in terms of gm/ml, the $IC_{50}$ values of the replicate lots ranged between 2.55 and $3.8 \times 10^{-9}$. Free RTA gave an $IC_{50}$ of about $3 \times 10^{-10}$ gm/ml. Within the limits of the assay, the lots with RTA:MoAb conjugation ratios of 3-3.4 gave the same $IC_{50}$ values. The $IC_{50}$ of the lot with the higher RTA:MoAb conjugation ratio was lower, although still within the range of five fold.

In order to determine if RTA activity was lost after conjugation to MoAb, these same values were expressed in terms of equivalent RTA molarity. Some loss of RTA activity with conjugation was seen in the lots with RTA:MoAb ration of 3, and more loss was noted in the lot with a RTA:MoAb ratio of 4. Other immunotoxins tested show no loss of RTA activity at conjugation ratios of 3.0. This suggest that the conjugated RTA remains biochemically active, but with higher conjugation there is steric hindrance of its activity.

c. Summary

The RLA assay demonstrates that little loss in activity of RTA is seen after conjugation. Since the production lot of immunotoxin had a higher conjugation ratio than the research lots, the $IC_{50}$ in terms of gm/ml was different. When expressed in terms of RTA molarity, however, the values are similar, although the lots with lower conjugation ratios have higher relative activity.

TABLE XVII

Reticulocyte Lysate Assay: $IC_{50}$ of Several Lots of XMMCO-791-RTA

| Lot # | RTA:IgG Ratio | Immunotoxin (gm/ml $IC_{50}$) | Equivalent RTA Molarity Immunotoxin* $IC_{50}$ | RTA Standard $IC_{50}$ |
|---|---|---|---|---|
| 51016A | 3.0 | $3.85 \times 10^{-9}$ | 51 pM | 5 pM |
| 51016B | 3.2 | $2.55 \times 10^{-9}$ | 35 pM | 5 pM |
| 51016C | 3.4 | $2.8 \times 10^{-9}$ | 41 pM | 5 pM |
| 51203 | 4.2 | $1.5 \times 10^{-8}$ | 134 pM | 8.1 pM |

*Calculated by multiplying the molarity of immunotoxin $IC_{50}$ by the number of RTA moieties per MoAb; e.g., Lot 51016A has an $IC_{50}$ of 11 pM and three RTA moieties/MoAb. Thus the equivalent RTA molarity is 51 pM.
The three replicate lots were reanalyzed three months after preparation and the results are shown in the following Table. Little loss of RTA activity is seen.

TABLE XVIII

| | Time after Production $IC_{50}$ gm/ml | |
|---|---|---|
| | 2 Weeks | 3 Months |
| 51016A | $3.8 \times 10^{-9}$ | $3.3 \times 10^{-9}$ |
| 51016B | $2.55 \times 10^{-9}$ | $3 \times 10^{-9}$ |
| 51016C | $2.8 \times 10^{-9}$ | $5.8 \times 10^{-9}$ |

4. Whole Cell Cytotoxicity Assay a. The Assay

This assay uses 791T as a positve cell line and MOLT-4 (A.T.C.C. Accession No. CRL 1582) as a negative cell line. It was designed to assess the ability of XMMCO-791-RTA to specifically kill cells expressing the gp72 antigen and is expressed as concentration of immunotoxin producing 50% inhibition of thymidine uptake. MOLT-4, a malignant T cell line lacking the gp72 antigen, is used as the negative cell line.

There are several tumor derived cell lines that carry the gp72 antigen and are specifically killed by XMMCO-791-RTA, as determined using various assays, all of which measure decreased protein synthesis ($^{75}$Se-Selenomethionine) or cell division (thymidine incorporation). Cell lines carrying the gp72 antigen include the colon carcinoma derived cell line C170, used in the flow cytometry analysis of various immunotoxin lots, and colon carcinoma derived cell line LS174.

791T cells or MOLT-4 cells were grown in serum-free medium for 4 to 7 days in T75 tissue culture flasks. 791T, an adherent cell line, was harvested using trypsin-EDTA (Gibco Labs) because it leaves the gp72 antigen intact. MOLT-4 is a suspension cell line. Cells were adjusted to the appropriate concentration, and the concentration used was related to the cells' rate of growth.

For convenience, the assay was carried out on cells in suspension. To prevent 791T cells from adhering during the assay, cells were plated into non-tissue culture coated NUNC 96-well round bottom plates, 100 μl/well to a final concentration of $2 \times 10^4$ cells/well (791T) or $4 \times 10^4$ cells/well (MOLT-4).

Immunotoxin dilutions were prepared using test tubes precoated with BSA. One hundred μl of each dilution were added to four wells containing cells, for final concentrations of 2.5 to 250,000 ng/ml. The RTA was diluted in a similar fashion to yield final concentrations of 500 μg/mg to 50 μg/ml. After a 48-hour incubation at 37° C. and 5% $CO_2$, 1 μCi of $^3H$-Thymidine was added to each well. After another 24-hour incubation, cells were harvested on filter pads and counted.

b. Results

Each assay of a lot included testing of the immunotoxin against 791T and MOLT-4 cells. Additionally, free RTA was sometimes tested against 791T cells. When the $IC_{50}$ values of immunotoxin or free RTA against 791T cells were compared in terms of RTA molarity, the $IC_{50}$ of the immunotoxin was more than three logs ($Log_{10}$) that of the free RTA. Also, there was a 3-$log_{10}$ difference between $IC_{50}$ of XMMCO-791-RTA immunotoxin against 791T and MOLT-4 cells. The $IC_{50}$ of XMMCO-791-RTA on negative control MOLT-4 cells (in RTA equivalents) was very similar to that of free RTA on 791T cells.

Table XIX summarizes the $IC_{50}$ of the replicate and production lots in terms of nanograms/ml and molarity of RTA. Although the $IC_{50}$ values were quite similar, there was a loss of potency as the conjugation ratio increased, reflected by a higher $IC_{50}$.

c. Summary

The whole cell kill assay measures the potency of intact immunotoxin. There was minimal lot to lot variability, as shown by the results with the three replicate lots. Even though the production lot had a decrease in binding due to the higher conjugation ratio, the $IC_{50}$ was still similar to those of the replicate lots. This may mean the decreased binding was somewhat compensated for by the increased number of RTA molecules. These $IC_{50}$ values were similar to those seen with other immunotoxins.

TABLE XIX

Cytotoxicity of Various lots of XMMCO-791 ($IC_{50}$)

| Lot | 791T | | | | MOLT-4 | | |
|---|---|---|---|---|---|---|---|
| | RTA:MoAB Ratio | ng/ml | Molarity ($10^{-11}$) | | ng/ml | Molarity ($10^{-11}$) | |
| | | | Immunotoxin | RTA | | Immunotoxin | RTA |
| 51016A | 3.0 | 6.9 | 2.9 | 8.7 | 11858 | 4.9 | 14700 |
| 51016B | 3.2 | 6.8 | 2.8 | 8.9 | 9614 | 3.9 | 12500 |
| 51016C | 3.4 | 9.6 | 3.8 | 12.9 | 12166 | 4.8 | 16400 |
| 51203 | 4.2 | 17.2 | 4.3 | 18.1 | 5903 | 3.5 | 14600 |

J. XMMCO-791-RTA Therapy of Human Tumor Xenografts

This study was performed to determine the therapeutic efficacy of XMMCO-791-RTA against human tumor xenografts expressing the gp72 antigen that is recognized by the XMMCO-791 antibody.

1. Procedure

Nude mice were implanted with tumor derived from an established xenograft according. (minced to small 1 mm pieces) Three to four days after tumor implantation, groups of up to 10 mice received immunotoxin by intraperitoneal injection and their tumor growth was compared with that in controls receiving saline. A range of treatment schedules, including daily injections for 20 days and a protocol involving treatment 3 times per weeks were employed.

2. Results

In all, three lots of immunotoxins were evaluated, Lots 41203B, 50903 and 51203.

There were three xenograft tests using two different conjugates. In the first series, XMMCO-791-RTA (Lot 41203B) was tested against osteogenic sarcoma 791T xenografts using various treatment protocols. One test scheduled treatment 3 times weekly at a dose of 4.8 mg/kg intraperitoneally for nine doses (total dose 43 mg/kg). Compared with the control group, this produced a significant inhibition of tumor growth (FIG. 1). The most effective response with this preparation was achieved in mice receiving eight doses of 12 mg/kg (total dose 96 mg/kg), administered at 2 to 3 day intervals. This is illustrated in FIG. 1c, showing that during the treatment there was a marked inhibition of tumor growth. As expected, tumor growth was observed in the treated group after cessation of treatment. In this respect, the rate of tumor growth in the treated group was comparable to that in the controls, although it was displaced in terms of tumor size. FIG. 1d summarizes these trials and shows a good correlation between total dose of XMMCO-791-RTA and therapeutic response, even though different dosing schedules were used.

The overall toxicities observed with this immunotoxin are summarized in FIG. 1e. As illustrated, there was no mortality with doses up to 100 mg/kg. The only observed effect was a gradual weight loss as doses escalated from 40 mg/kg to 100 mg/kg.

In the second series of trials using XMMCO-791-RTA (Lot 50903), the treatment schedule was 5 mg/kg daily for 20 days (total dose 100 mg/kg). This protocol produced marked inhibition in growth of sarcoma derived 791T xenografts (FIG. 2a) and colon carcinoma derived C170 xenografts (FIG. 2b). There was significant toxicity, however, with 3/10 mice dying in both tests.

Taking into consideration the experience gained with two immunotoxin preparations, a third series of test were carried out using XMMCO-791-RTA (Lot 51203). The immunotoxin was given in 20 daily doses of 3 mg/kg/day (total dose 60 mg/kg); the response elicited against colon carcinoma C170 xenografts demonstrated significant suppression of tumor growth. This is illustrated in FIG. 3 which shows growth of colon carcinoma C170 xenografts in immunotoxin-treated mice compared with controls. Furthermore, tumor weights in the immunotoxin treated group were significantly less than those in controls (T/C=0.52 p <0.02) at the completion of the trial.

EXAMPLE II-XMMCO-228RTA CONJUGATES

A. Production of Hybridomas

Balb/c mice (Bantin & Kingman, U.K.) were immunized with carcinoembryonic antigen (CEA) derived from a perchlorate extract of a colon carcinoma liver metastasis. The immunization schedule consisted of 10 μg CEA in complete Freund's adjuvant (CFA) given intraperitoneally on Days 0 and 7, and 20 μg of CEA (Also in CFA) given intraperitoneally on Days 25, 56 and 63.

Three days after the last antigen boost, spleen cells from an immunized mouse were aseptically removed. Following procedures as outlined elsewhere (Galfre et al (1977) Nature 266: 550, which is incorporated by reference), $10^6$ spleen cells were fused with $10^6$ cells of P3-NSI-Ag4-1 (A.T.C.C. Accession No. TIB-18), a hypoxanthine-methotrexate-thymidine (HMT) sensitive murine myeloma cell line. Using polyethylene glycol (PEG), hybrid cells were placed into 96-well culture plates, (Costar, Cambridge, MA #3596) on medium containing a feeder layer of rat peritoneal exudate cells ($2.5 \times 10^3$ cells/well). Cells were cultured in Dulbecco's Modified Eagle's Medium (Flow Labs, Irvine, U.K.) containing 15% Fetal Calf Serum (Myoclone, Gibco, Paisley, U.K.) and hypoxanthine ($10^{-4}$M), thymidine ($1.6 \times 10^{-5}$M) (both from Sigma, Dorset, U.K.) and methotrexate ($10^{-5}$M) (Lederle, Hampshire, U.K.).

Within two weeks post fusion, cultures of hybridoma cells were tested for antibody binding to CEA by enzyme immunoassay (EIA). Cultures that were positive were cloned using limiting dilution, plating 1-3 cells/well into 96 well culture plates. Wells containing only one colony were identified by microscopic examination, then tested for reactivity with CEA and normal colon antigen (NCA) by EIA and radioimmunoassay (RIA), and for reactivity on extranuclear membranes from primary colorectal tumors and normal colon by EIA. The clone designated XMMCO-228 was found to stably secrete immunoglobulin which was determined to be of the IgG2a subclass by solid phase RIA using standard methods. Hybridoma XMMCO-228 is presently on deposit with the American Type Culture Collection (A.T.C.C.), 12301 Parklawn Dr., Rockville, MD 20852, USA. The deposit was made on Aug. 14, 1986, and given A.T.C.C. Accession No. HB 9174.

Balb/c mice (Bantin & Kingman, U.K.), 6–10 weeks old, were used to culture the hybridoma peritoneally. Approximately $10^7$ hybridoma cells were injected into mice that had been pretreated 3 weeks earlier with 0.5 mls of pristane (Aldridge, Gillingham, Dorset, U.K.) injected intraperitoneally (i.p.). The resultant ascites fluid, collected 3 weeks after injection of the hybridomas, contained on average 5 mg/ml of the antibody as determined by measuring immunoglobulin level according to the method of Price and Baldwin *ICRS Med. Sci.*, (1984) 12: 1000-01, which is incorporated by reference.

The antibody in ascites fluid was purified by affinity chromatography using a Sepharone-Protein A column using methods well known by those skilled in the art.

The hybridoma was grown in vitro in Dulbecco's Minimal Essential Medium (Flow Labs, Irvine, U.K.) with 10% Fetal Calf Serum (Myoclone, Gibco, Paisley, U.K.) and hypoxanthine ($10^{-4}$M), thymidine ($1.6 \times 10^{-5}$M) (both from Sigma, Dorset, U.K.) and methotrexate ($10^{-5}$M) (Lederle, Hampshire, U.K.) in plastic 300 ml bottles. Cell concentration was $10^5$ cells/ml medium over a culturing period of 4–5 days, with a MoAb concentration of 4 µg/ml medium, and a doubling time of 12 hours. compared to E5).

B. In Vitro Antibody Binding to Cell Lines Measured by Flow Cytometry

The binding of XMMCO-228 and XMMCO-791 MoAbs to MKN45 cells was determined by flow cytometry employing methods well known to those skilled in the art and described above. The gastric carcinoma cell line MKN45 expresses both the 72kD antigen with which the XMMCO-791 MoAb reacts and the CEA antigen with which XMMCO-228 reacts. B14/B8 is a MoAb directed against breast cancer, which reacts with the normal color antigen (NCA) subsection of the CEA antigen. Normal mouse serum was used as a control. The results are summarized in Table XX.

TABLE XX

| Binding to MKN45 Cells by Flow Cytometry | |
|---|---|
| MoAb | Mean Fluorescence Intensity |
| XMMCO-228 | 987 |
| B14/B8 | 790 |
| XMMCO-791 | 485 |
| Control | 15 |

C. In Vivo Antibody Binding to Normal Tissues Measured by Immunoperoxidase

The technique for Indirect Immunoperoxidase staining has been described above. Table XXI is a summary of the results obtained with XMMCO-228 MoAbs in humans:

TABLE XXI

| Antibody Binding to Normal Tissues Measured by Immunoperoxidase | |
|---|---|
| COLORECTAL CANCER: | 5/5 intense staining of Ca |

TABLE XXI-continued

| Antibody Binding to Normal Tissues Measured by Immunoperoxidase | |
|---|---|
| NORMAL COLON | 90% + of population staining +) 5/5 intense staining of glandular epith., especially intense apical staining |
| AUTOPSY TISSUE: | Negative tissue— Kidney Pancreas Muscle Liver Skin Heart Testis Spleen Spinal Cord Stomach Aorta Cerebellum Lymph Node Questionable (+/−) Lung Positive— Esophagus (+ squamous epith) |

NOTE:
glucose oxidase method showed that Ab. 228 does not stain granulocytes. Almost every other antibody that we have studied that is similar to CEA has stained granulocytes.

It is significant that XMMCO-228 MoAbs do not bind to granulocytes. Normal colon antigen (NCA) appears on such diverse tissues as normal colon, granulocytes, and progenitor bone marrow cells. Because the CEA antigen has a NCA subsection, many anti-CEA MoAbs also bind the NCA on various normal tissues, which XMMCO-228 MoAbs do not.

D. XMMCO-228 Ricin Toxin A Chain (RTA) Conjugates

As in the case of XMMCO-791-RTA conjugates described above, the conjugation technique, including purification of the A chain of ricin, is disclosed in U.S. Pat. No. 4,590,071, the disclosures of which are hereby incorporated by reference.

E. XMMCO-228-RTA In Vitro Cytotoxicity

In vitro cytotoxicity of XMMCO-228-RTA conjugates was determined by the $^{75}$Se-Selenomethionine Assay. Single cell suspensions of gastric carcinoma derived MKN45 cells were inoculated with immunotoxin or RTA for 15 minutes, washed and added to flat bottomed microtiter plates at a concentration of $10^5$ cells/0.2 ml of immunotoxin or RTA in RPMI medium containing 10% fetal calf serum. Various amounts of immunotoxin were added to each well. Twenty-four hours later, $^{75}$Se-Selenomethionine was added to each well. Cultures were further incubated for 16 hours, washed, dried on the bottom of the wells, and the wells were counted in a gamma counter. The results are summarized in Table XXII, expressed in terms of 50% inhibition concentration.

TABLE XXII

| In Vitro Cytotoxicity Against MKN45 Cells | |
|---|---|
| Agent | IC$_{50}$ (ng/ml) |
| RTA | 2238 |
| XMMCO-791-RTA | 1000 |
| XMMCO-228-RTA | 600 |
| XMMCO-791-RTA + XMMCO-228-RTA (50%/50% mixture) | 560 |
| Agent | IC$_{50}$ (molarity)* |
| RTA | $1 \times 10^{-8}$M |
| XMMCO-791-RTA | $3.5 \times 10^{-10}$M |
| XMMCO-228-RTA | $1 \times 10^{-10}$M |

TABLE XXII-continued

| In Vitro Cytotoxicity Against MKN45 Cells | |
|---|---|
| XMMCO-791-RTA + XMMCO-228-RTA (50%/50% mixture) | $3.5 \times 10^{-10}$M |

*Adjusted for equivalent RTA molarity

These data indicate that when XMMCO-791-RTA and XMMCO-228-RTA are administered in a "cocktail" form, the cytotoxicity is at least additive, and possibly synergistic. They also show the efficacy of immunotoxin (or antibody directed RTA) compared to RTA alone.

F. XMMCO-228-RTA Therapy of Human Tumor Xenografts

For each data point, 7–10 nude mice were implanted with LS174T cells, a human colon adenocarcinoma derived cell line (A.T.C.C. Accession No. CL 188). Three days post-implant, the first dose of the treatment compound was administered, followed by 10–20 doses until the schedule dose was completed. The results are summarized in Table XXIII, expressed as a ration of the tumor weight in treated mice divided by the tumor weight in control (untreated) mice. The results, in terms of mean tumor diameter, are summarized graphically in FIG. 4.

TABLE XXIII

Therapy of Human Tumor Xenografts With XMMCO-228-RTA

| Expt. | Xenograft Tumor | Treatment Compound | Schedule Dose mg/kg | Response: Tumor Weight Treated / Tumor Weight Control |
|---|---|---|---|---|
| 1 | LS 174T | RTA | 20 | 0.70 |
| 2 | LS 174T | XMMCO-228 | 80 | 1.18 |
| 3 | LS 174T | XMMCO-228-RTA | 56 | 0.36 |

These results demonstrate the efficacy of XMMCO-228-RTA in the therapy of human tumor xenografts.

tomed microtiter plates at a concentration of $10^5$ cells/0.2 ml of immunotoxin or RTA in RPMI medium containing 10% fetal calf serum. Various amounts of immunotoxin were added to each well. Twenty-four hours later, $^{75}$Se-Selenomethionine was added to each well. Cultures were further incubated for 16 hours, washed, dried on the bottom of the wells, and the wells were counted in a gamma counter. The results are summarized in Table XXII above, expressed in terms of 50% inhibition concentration.

These data indicate that when XMMCO-791-RTA and XMMCO-228-RTA are administered in a "cocktail" form, the cytotoxicity is at least additive, and possibly synergistic. They also show the efficacy of immunotoxin (or antibody) directed RTA compared to RTA alone.

C. XMMCO-791-RTA+XMMCO-228-RTA Conjugate Cocktail Therapy of Human Tumor Xenografts For each data point, 7–10 nude mice were implanted with MKN 45 cells, derived cell line. Three days post-implant, the first dose of the treatment compound was administered, followed by 10–20 doses until the scheduled dose was completed. The results are summarized in Table XXIV, expressed as a ratio of the tumor weight in treated mice divided by the tumor weight in control (untreated) mice.

TABLE XXIV

Therapy of Human Tumor Xenografts With XMMCO-228-RTA

| Expt. | Xenograft Tumor | Treatment Compound | Schedule Dose mg/kg | Response: Tumor Weight Treated / Tumor Weight Control |
|---|---|---|---|---|
| 1 | MKN 45 | XMMCO-228-RTA | 25 | 0.74 |
|   |   | XMMCO-228 | 25 | 1.1 |
| 2 | MKN 45 | XMMCO-228-RTA + XMMCO-791-RTA | * | 0.56 |

*25 mg/kg each of XMMCO-228-RTA and XMMCO-791-RTA administered as a mixture.

EXAMPLE III-XMMCO-791-RTA AND XMMOC-228-RTA COCKTAILS

A. XMMCO-791-RTA+XMMCO-228-RTA Conjugate Cocktails

A cocktail of XMMCO-791-RTA and XMMCO-228-RTA consists of a mixture of XMMCO-791-RTA and XMMCO-228-RTA, in any ratio, and administered to a cancer cell host in a dose range of about 0.01 mg/kg/day to 20.0 mg/kg/day. The cocktail is administered perenterally, generally by intravenous infusion or intrapercitoneal injection in a suitable vehicle, such as phosphate buffered saline or the like.

B. In Vitro Cytotoxicity of Conjugate Cocktails

In vitro cytotoxicity of XMMCO-228-RTA conjugates was determined by the $^{75}$Se-Selenomethionine assay. Single cell suspensions of gastric carcinoma derived MKN45 cells were inoculated with immunotoxin or RTA for 15 minutes, washed and added to flat bot- These data indicate that when XMMCO-791-RTA and XMMCO-228-RTA are administered in a "cocktail" form, the cytotoxicity is at least additive, and possibly synergistic. They also show the efficacy of a cocktail consisting of XMMCO-791-RTA and XMMCO-228-RTA in treating cancer cells in a host.

The present invention provides efficacious, novel compounds and methods for the therapy of various cancer cells. The cytotoxic conjugates are particularly efficacious when administered in cocktail form.

Although the present invention has been described in some detail by way of illustration and example for purposes of clarity of understanding, it will be obvious that certain changes and modifications may be practiced within the scope of the appended claims.

What is claimed is:

1. A pharmaceutical composition comprising an immunotoxin consisting essentially of a ribosomal inhibiting toxin conjugated to a monoclonal antibody that binds to an epitope on a non-shedding membrane-bound human osteogenic sarcoma tumor associated antigen of about 72 kD m.w., and which has the binding specificity of antibodies produced by hybridoma XMMCO-791 having A.T.C.C. Accession No. HB 9173.

2. The composition according to claim 1 wherein the immunoglobulin is produced by hybridoma XMMCO-791 having A.T.C.C. Accession No. HB 9173.

3. A pharmaceutical composition comprising an immunotoxin consisting essentially of a ribosomal inhibiting toxin conjugated to a monoclonal antibody that binds to an epitone on a carcinoembryonic antigen of about 180 kD m.w. present on human colon carcinoma cells, and which has the binding specificity of antibodies produced by hybridoma XMMCO-228 having A.T.C.C. Accession No. HB 9174.

4. The formulation according to claim 3, wherein the immunoglobulin is produced by hybridoma XMMCO-228 having A.T.C.C. Accession No. HB 9174.

5. The composition according to claims 1 or 3, wherein the ribosomal inhibiting protein is a lectin A chain purified with anti-lectin B chain antibodies.

6. The composition according to claim 5, wherein the lectin A chain is ricin A chain purified with anti-ricin B chain antibodies.

7. The composition according to claim 5, wherein the lectin A chain is abrin A chain purified with anti-abrin B chain antibodies.

8. A cytotoxic therapeutic cocktail comprising a mixture of:
   a first immunotoxin consisting essentially of a ribosomal inhibiting toxin conjugated to a monoclonal antibody that binds to an epitope on a non-shedding human osteogenic sarcoma tumor associated antigen of about 72 kD m.w., which has the binding specificity of antibodies produced by hybridoma XMMCO-791 having A.T.C.C. Accession No. HB 9173; and
   a second immunotoxin consisting essentially of a ribosomal inhibiting toxin conjugated to monoclonal antibody that binds to an epitope on a carcinoembryonic antigen of 180 kD m.w. present on human colon carcinoma cells, and which has the binding specificity of antibodies produced by hybridoma XMMCO-228 having A.T.C.C. Accession No. HB 9174.

9. The cytotoxic cocktail according to claim 8, wherein the monoclonal antibody of the first immunotoxin is that produced by hybridoma XMMCO-791 having A.T.C.C. Accession No. HB 9174.

10. The cytotoxic cocktail according to claim 9, wherein the monoclonal antibody of the second immunotoxin is that produced by hybridoma XMMCO-228 having A.T.C.C. Accession No. HB 9174.

11. The cytotoxic cocktail according to claim 8, wherein the ribosomal inhibiting protein is a lectin A chain purified with anti-lectin B chain antibodies.

12. The cytotoxic cocktail according to claim 11, wherein the lectin A chain is ricin A Chain purified with anti-ricin B chain antibodies.

13. The cytotoxic cocktail according to claim 11, wherein the lectin A chain is abrin A Chain purified with anti-abrin B chain antibodies.

14. The cytotoxic cocktail according to claim 11, wherein the lectin A chain of the first conjugate is ricin A chain purified with anti-ricin B chain antibodies and the lectin A chain of the second conjugate is abrin A chain purified with anti-abrin B chain antibodies.

15. A method for the treatment of cancer cells selected from the group consisting carcinoma and sarcoma type cancer cells, comprising administering a therapeutic dose of a pharmaceutical composition according to claim 1 to a cancer cell host wherein said cells express the defined epitope.

16. A method for the treatment of cancer cells selected from the group consisting carcinoma and sarcoma type cancer cells, comprising administering a therapeutic dose of a pharmaceutical composition according to claim 3 to a cancer cell host wherein said cells express the defined epitope.

17. A method for the treatment of cancer cells, selected from the group consisting carcinoma and sarcoma type cancer cells, comprising administering a therapeutic dose of the cytotoxic cocktail according to claim 8 to a cancer cell host wherein said cells express the defined epitope.

18. The method for the treatment of cancer cells according to either of claims 15 or 16, wherein the therapeutic dose of the cytotoxic conjugate is approximately 0.01 mg to 20.0 mg per kg of host body weight per day.

19. The method for the treatment of cancer cells according to either of claims 15 or 16, wherein the therapeutic dose of the cytotoxic conjugate is approximately 0.05 mg to 5.0 mg per kg of host body weight per day.

20. The method for the treatment of cancer cells according to claim 17, wherein the therapeutic dose of the cytotoxic conjugates is approximately 0.01 mg to 20.0 mg per kg of host body weight per day.

21. The method for the treatment of cancer cells according to claim 17, wherein the therapeutic dose of the cytotoxic conjugates is approximately 0.05 mg to 5.0 mg per kg of host body weight per day.

22. The method for the treatment of cancer cells according to any of claims 15, 16, or 17, wherein the cancer cells are colon carcinoma cells.

23. The method for the treatment of cancer cells according to any of claims 15, 16, or 17, wherein the cancer cells are ovarian carcinoma cells.

24. The method for the treatment of cancer cells according to claim 15, wherein the cancer cells are osteogenic sarcoma cells.

25. Hybridoma XMMCO-228 having A.T.C.C. Accession No. HB 9174 which produces an immunoglobulin that defines an epitope on carcinoembryonic antigen.

26. A kit for the treatment of cancer cells, comprising compositions according to any of claims 1, 3 or 8.

27. A method according to claim 15, 16 or 19 wherein the cancer cell host is a human.

28. The cytotoxic cocktail according to claim 8, wherein the first immunotoxin and second immunotoxin are each present at about 50% by weight.

* * * * *